United States Patent
Leung et al.

(10) Patent No.: US 11,958,868 B2
(45) Date of Patent: Apr. 16, 2024

(54) METHODS OF USING METAL COMPLEXES TO PROMOTE WOUND HEALING

(71) Applicants: University of Macau, Macau (CN); Hong Kong Baptist University, Hong Kong (CN)

(72) Inventors: Chung Hang Leung, Macau (CN); Dik Lung Ma, Hong Kong (CN); Ligen Lin, Macau (CN); Guodong Li, Macau (CN); Chung Nga Ko, Hong Kong (CN); Dan Li, Macau (CN); Chao Yang, Macau (CN)

(73) Assignees: University of Macau, Macau (CN); Hong Kong Baptist University, Hong Kong (CN)

( * ) Notice: Subject to any disclaimer, the term of this patent is extended or adjusted under 35 U.S.C. 154(b) by 0 days.

(21) Appl. No.: 17/805,747

(22) Filed: Jun. 7, 2022

(65) Prior Publication Data

US 2023/0391810 A1    Dec. 7, 2023

(51) Int. Cl.
*A61K 31/555* (2006.01)
*A61P 17/02* (2006.01)
*C07F 15/00* (2006.01)

(52) U.S. Cl.
CPC .......... *C07F 15/0033* (2013.01); *A61P 17/02* (2018.01); *C07F 15/0073* (2013.01)

(58) Field of Classification Search
CPC .......... A61K 31/555; A61P 17/02; C12Q 1/00

USPC .......................................... 514/185; 435/184
See application file for complete search history.

(56) References Cited

U.S. PATENT DOCUMENTS 5,474,765 A * 12/1995 Thorpe .................. A61K 47/58
424/78.17

OTHER PUBLICATIONS

Cao, R. et al.: Membrane localized Iridium (III) complex induces endoplasmic reticulum stress and mitochondria-mediated apoptosis in human cancer cells. J. med. Chem., vol. 56, pp. 3636-3644, 2013.*
Graf, M. et al.: Photophysical and biological characterization of new cationic cyclometallated M(III) complexes of rhodium and iridium. J. of Organometallic Chem., vol. 7651, pp. 46-52, 2014.*
Kang, T-S. et al.: Identification of IIIIIridium (III) based inhibition of tumor necrosis factor-alpha. J. Med. Chem., vol. 59, pp. 4026-4031, 2016.*
Kang, T-S. et al.: A rhodium (III) based inhitor of autotaxin with antiproliferative activity. Biochimica et Biophys. Acta, vol. 1861, pp. 256-263, 2017.*

* cited by examiner

*Primary Examiner* — Charanjit Aulakh
(74) *Attorney, Agent, or Firm* — S&F/WEHRW

(57) ABSTRACT

Method of inhibiting a protein-protein interaction between Von Hippel-Lindau tumor-suppressor protein and hypoxia-inducible factor 1-alpha useful in the treatment of angiogenesis-related diseases and promoting wound healing.

8 Claims, 14 Drawing Sheets

Specification includes a Sequence Listing.

METHODS OF USING METAL COMPLEXES TO PROMOTE WOUND HEALING

TECHNICAL FIELD

The present disclosure relates to methods of inhibiting the activity of hypoxia-inducible factor 1-alpha (HIF-1α) using metal complexes. The methods described herein are useful in the treatment of angiogenesis-related diseases and promoting wound healing, particularly in diabetic subjects.

BACKGROUND

Poor wound healing, especially in diabetic patients, leads to substantial morbidity and mortality and can have a far-reaching socioeconomic impact. The annual worldwide market for advanced wound healing products for hard-to-heal wounds and scars exceeds US$5 billion. Wound healing in diabetic patients can be compromised due to impaired wound contraction, reduced blood supply, and infection. To date, several treatment strategies for diabetic wounds are available, including regular debridement, surgical revascularization, infection therapy, pressure-offloading and bioengineered alternative tissue products. However, most treatments are effective only for mild to moderate wounds and are not 100% effective in preventing the risk of amputation and recovering full skin functionalities. Therefore, the development of novel drugs or therapies for the treatment of diabetic wound healing in clinical practice is desperately needed.

Wound healing is a systematic and dynamic process involving epithelialization, angiogenesis, granulation tissue formation, and wound contraction, all of which are regulated by HIF-1α. In normal tissues, HIF-1α steady-state levels are low due to oxygen-dependent hydroxylation of HIF-1α by prolyl hydroxylase domain proteins (PHDs). This allows HIF-1α to combine with Von Hippel-Lindau (VHL) tumor-suppressor protein to generate a complex that is readily recognized by the proteasome and rapidly degraded. Currently, several reported inhibitors of PHDs as stabilizers for HIF-1α have entered clinical trials for the treatment of chronic anemia. However, PHDs inhibitors are associated with side effects, such as fatal liver necrosis, raising concerns about their safety and tolerability for widespread use.

Protein-protein interactions (PPIs) are attractive targets in drug discovery. For example, venetoclax, a B-cell lymphoma (BCL)-2 inhibitor used for the treatment of chronic lymphocytic leukemia (CLL), was the first small molecule inhibitor of PPIs approved by the FDA. Ciulli and co-workers were the first to report a bona-fide VHL-HIF-1α protein-protein interaction inhibitor VH298 as a high-quality chemical probe of the HIF signaling cascade in the hypoxia signaling pathway. This inhibitor represented an attractive starting point to the development of potential new therapeutics targeting hypoxia signaling.

Over the last decade, metal-based compounds possessing several promising advantages have been explored for targeting PPIs. Metal complexes, with their high structural diversity and readily tunable steric and electronic properties, can adopt a wide range of geometrical shapes based on the oxidation state of their metal center, and the nature of their co-ligands. The sophisticated three-dimensional geometries available to transition metal complexes might allow them to be more effective in generating compounds with suitable shapes and functional groups that are complementary to the binding regions of PPI surfaces.

World diabetes patients are expected to reach 400 million by 2030. Wound healing complications, leading to foot ulcers or even amputation, are a major factor contributing to diabetes-induced mortality. Therefore, novel drugs are needed for promoting wound healing, particularly in diabetic patients. HIF-1α is critical in wound healing because it plays a key role in regulating vital processes involved in tissue repair. PHD inhibitors have been previously developed as HIF-1α stabilizers. Several PHDs inhibitors have been introduced into clinical trials for anemia or ischemia, including BAY-853934, FG-4592, FG-2216 and GSK1278863. Of these, FG-4592 has entered phase 3 trials to treat anemia in patients with chronic kidney disease. The effectiveness of PHDs inhibitors in clinical trials demonstrates that HIF-1α signaling can serve as a drug target for angiogenesis-related diseases. However, there are a few disadvantages to PHDs inhibitors, such as poor target selectivity and adverse side effects. For example, during a phase 2 trial of FG-2216, many patients exhibited abnormal liver enzyme test results and one patient developed fatal hepatic necrosis. Previous studies have shown that hyperglycemia destabilizes HIF-1α and impairs its function in diabetes mouse through a VHL-dependent mechanism. Thus, an alternative strategy to stabilize HIF-1α via blocking the downstream interaction of HIF-1α and VHL is a potentially superior strategy to inhibiting upstream PHDs, in order to avoid HIF-independent off-target effects as has been observed with PHD inhibitors in clinical development. In this context, interrupting the VHL-HIF-1α protein-protein interaction may be a highly effective strategy for the treatment of diabetic wounds. Until now, few inhibitors of the interaction between VHL and HIF-1α have been discovered, and only VH298 has been reported to promote enthesis healing and wound healing in vivo.

There thus exists a need for improved methods for inhibiting the activity of HIF-1α, treating angiogenesis-related diseases, and promoting wound healing, particularly in the treatment of diabetic wounds, that address or overcome some of the challenges described above.

SUMMARY

Disclosed herein are methods for promoting wound healing with metal complexes, such as iridium(III) and rhodium(III) complexes, which act as potent inhibitors of the VHL-HIF-1α PPI, which can effectively induce the accumulation of HIF-1α in cellulo and in vivo. The potential of metal complexes described herein in wound healing in three diabetic mouse models (including db/db, HFD/STZ and STZ models) were evaluated, demonstrating that the blocking of the VHL and HIF-1α interaction is a viable strategy for treating diabetic ulcers.

In a first aspect, provided herein is a method of inhibiting a protein-protein interaction between Von Hippel-Lindau (VHL) tumor-suppressor protein and hypoxia-inducible factor 1-alpha (HIF-1α) in a subject in need thereof, the method comprising: administering a therapeutically effective amount of a compound comprising a metal complex of Formula 1 and a pharmaceutically acceptable anion, wherein the metal complex of Formula 1 has the structure:

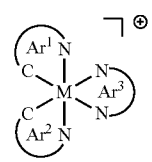

1 wherein M is Ir (III) or Rh (III);
each of Ar¹ and Ar² is independently selected from the group consisting of:

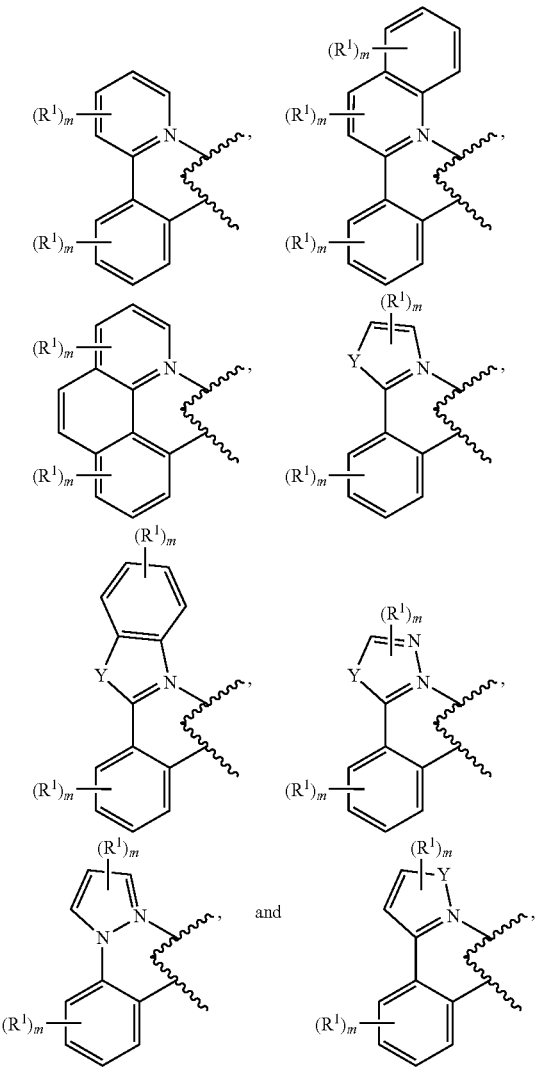

wherein m for each instance is independently a whole number selected from 0-2;
Y is S or O; and
R¹ for each instance is independently selected from the group consisting of halide, nitro, nitrile, azido, —OR³, —OP(O)(OR³)₂, —SR³, —N(R³)₂, —P(O)(OR³)₂, —C(O)R³, —C(O)OR³, —OC(O)R³, —N(R³)C(O)R³, —C(O)N(R³)₂, —N(R³)C(O)OR³, —OC(O)N(R³)—, —OC(O)OR³, —N(R³)C(O)N(R³)₂, —S(O)₂R³, —S(O)₂OR³, —S(O)₂N(R³)₂, —N(R³)S(O)₂R³, alkyl, haloalkyl, perhaloalkyl, alkenyl, alkynyl, cycloalkyl, heterocycloalkyl, aryl, heteroaryl, aralkyl, and —(CR⁴₂)ₚA, wherein p for each instance is independently a whole number selected from 1-10; R⁴ for each instance is hydrogen, alkyl, cycloalkyl, aryl, or heteroaryl; and A for each instance is independently halide, nitrile, nitro, azido, —OR³, —SR³, —N(R³)₂, —C(O)R³, —C(O)OR³, —OC(O)R³, —N(R³)C(O)R³, —C(O)N(R³)₂, —N(R³)C(O)OR³, —OC(O)N(R³)—, —OC(O)OR³, —N(R³)C(O)N(R³)₂, —S(O)₂R³, —S(O)₂N(R³)₂, —N(R³)S(O)₂R³, alkynyl, heterocycloalkyl, aryl, heteroaryl, and aralkyl; or two instances of R¹ together with the carbons to which they are bonded form an optionally substituted 5-6 membered carbocycle;
Ar³ is selected from the group consisting of:

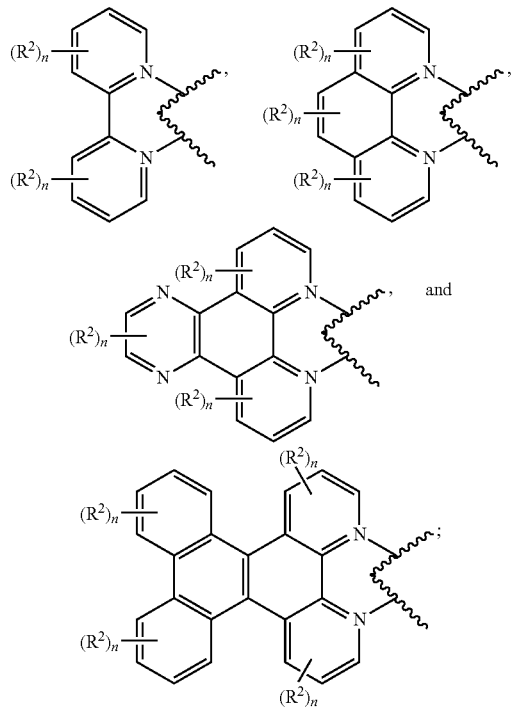

wherein n for each instance is independently a whole number selected from 0-2;
R² for each instance is independently selected from the group consisting of halide, nitro, nitrile, azido, —OR³, —OP(O)(OR³)₂, —SR³, —N(R³)₂, —P(O)(OR³)₂, —C(O)R³, —C(O)OR³, —OC(O)R³, —N(R³)C(O)R³, —C(O)N(R³)₂, —N(R³)C(O)OR³, —OC(O)N(R³)—, —OC(O)OR³, —N(R³)C(O)N(R³)₂, —S(O)₂R³, —S(O)₂OR³, —S(O)₂N(R³)₂, —N(R³)S(O)₂R³, alkyl, haloalkyl, perhaloalkyl, alkenyl, alkynyl, cycloalkyl, heterocycloalkyl, aryl, heteroaryl, aralkyl, and —(CR⁴₂)ₚA, wherein p for each instance is independently a whole number selected from 1-10; R⁴ for each instance is selected from the group consisting of hydrogen, alkyl, cycloalkyl, aryl, and heteroaryl; or two instances of R⁴ taken together with the carbon to which they are bonded form a 3-6 membered cycloalkyl; and A for each instance is independently selected from the group consisting of halide, nitrile, nitro, azido, —OR³, —SR³, —N(R³)₂, —C(O)R³, —C(O)OR³, —OC(O)R³, —N(R³)C(O)R³, —C(O)N(R³)₂, —N(R³)C(O)OR³, —OC(O)N(R³)—, —OC(O)OR³, —N(R³)C(O)N(R³)₂, —S(O)₂R³, —S(O)₂N(R³)₂, —N(R³)S(O)₂R³, alkynyl, heterocycloalkyl, aryl, heteroaryl, and aralkyl; or two instances of R² together with the carbons to which they are bonded form an optionally substituted 5-6 membered carbocycle; and
R³ for each instance is independently hydrogen, alkyl, haloalkyl, perhaloalkyl, alkenyl, alkynyl, cycloalkyl, heterocycloalkyl, aryl, heteroaryl, or aralkyl; or two instances of $R^3$ together with the atoms to which they are bonded form a 3-6 membered cycloalkyl or heterocycloalkyl.

In certain embodiments, the subject has an angiogenesis-related disease.

In certain embodiments, the angiogenesis-related disease is selected from the group consisting of impaired wound healing, age-related macular degeneration, diabetic retinopathy, glaucoma, restenosis, atherosclerosis, psoriasis, rheumatoid arthritis, inflammation, endometriosis, and hemangioma.

In certain embodiments, each instance of $R^1$ is independently selected from the group consisting of alkyl, halide, and $-OR^3$.

In certain embodiments, each of $Ar^1$ and $Ar^2$ is independently selected from the group consisting of:

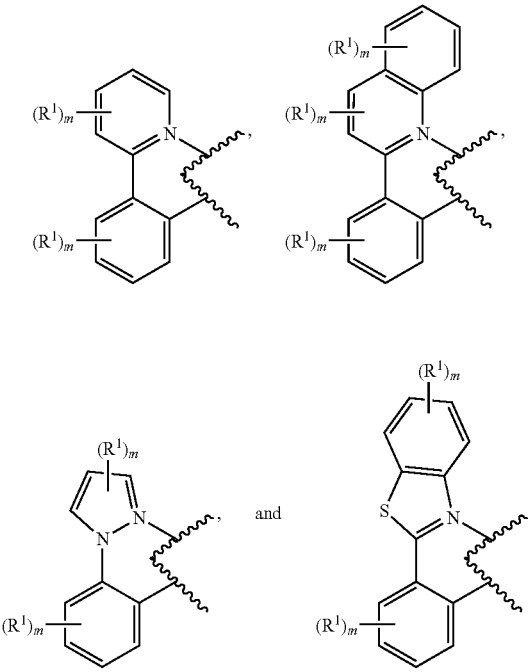

In certain embodiments, each instance of $R^1$ is independently selected from the group consisting of alkyl, halide, and $-OR^3$.

In certain embodiments, each of $Ar^1$ and $Ar^2$ is:

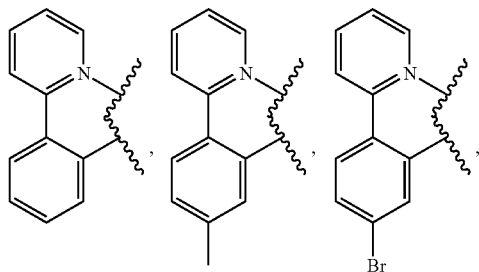

-continued

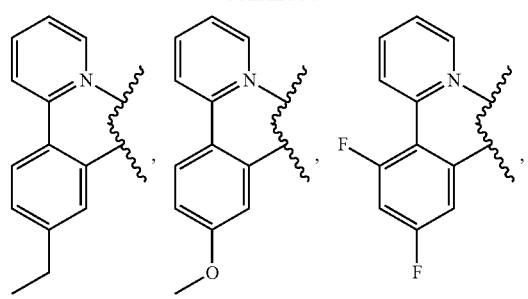

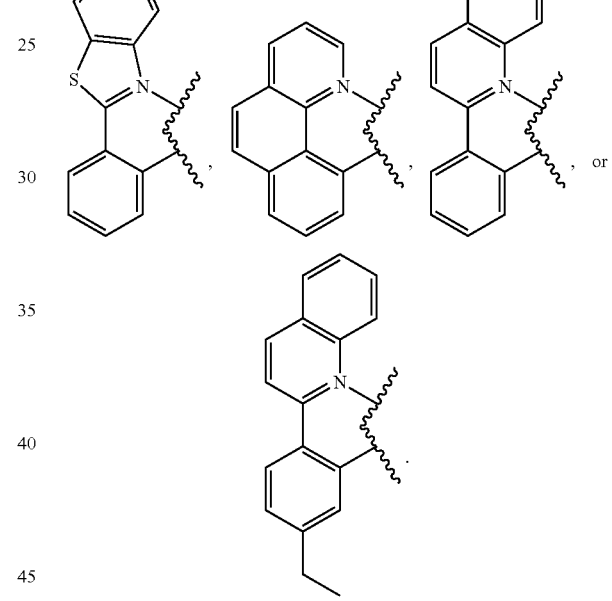

In certain embodiments, each instance of $R^2$ is independently selected from the group consisting of alkyl, aryl, halide, nitro, $-OR^3$, $-P(O)(OR^3)_2$, and $-C(O)OR^3$; or two instances of $R^2$ taken together with the carbon to which they are bonded form a 6 membered cycloalkyl.

In certain embodiments, $Ar^3$ is selected from the group consisting of:

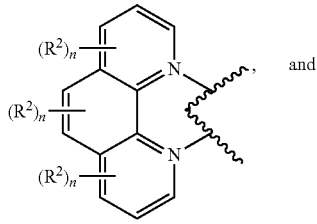

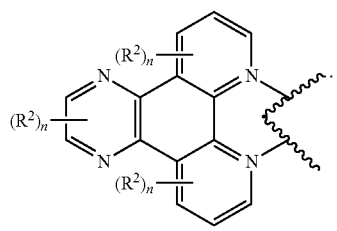
In certain embodiments, each instance of $R^2$ is independently selected from the group consisting of alkyl, halide, phenyl, and —$OR^3$; or two instances of $R^2$ taken together with the carbon to which they are bonded form a 6 membered cycloalkyl.
In certain embodiments, $Ar^3$ is.
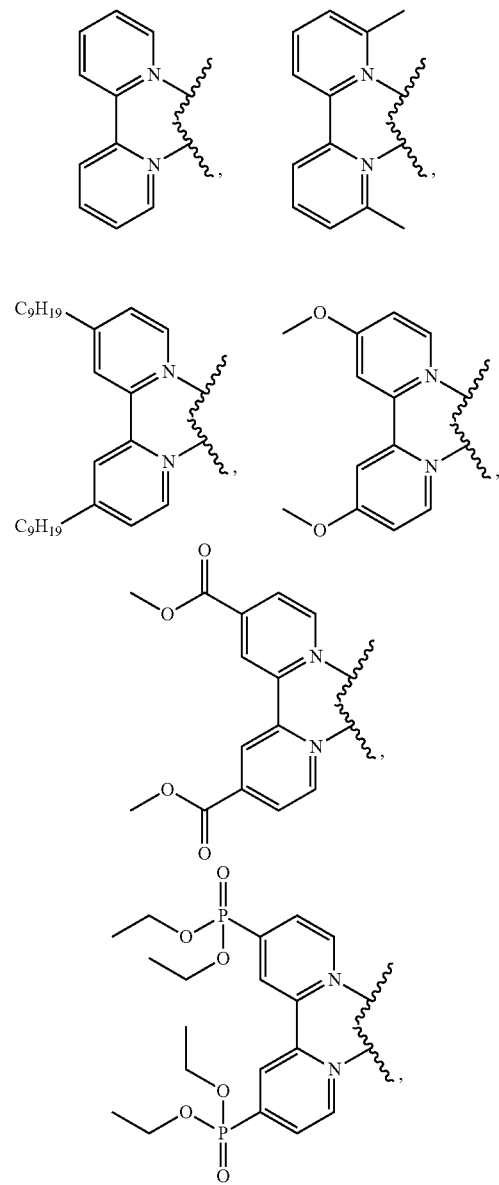
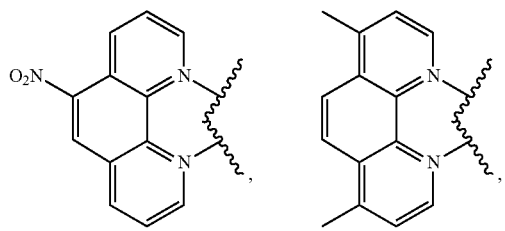
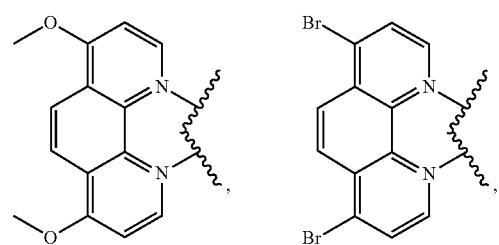
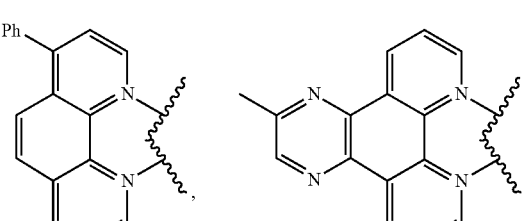
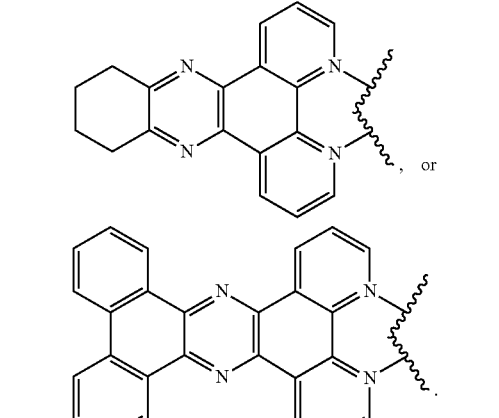
In certain embodiments, each of $Ar^1$ and $Ar^2$ is:
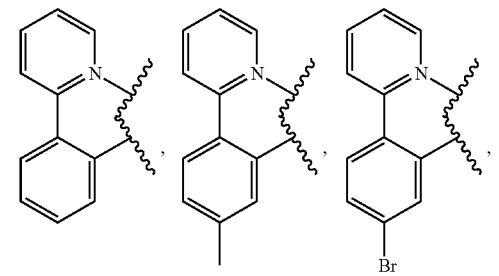

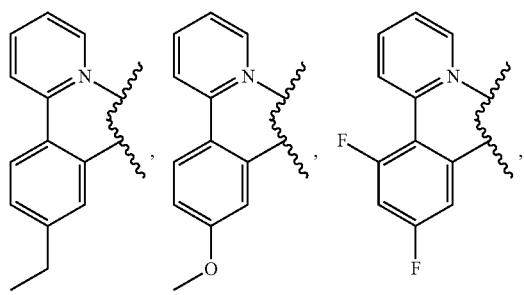
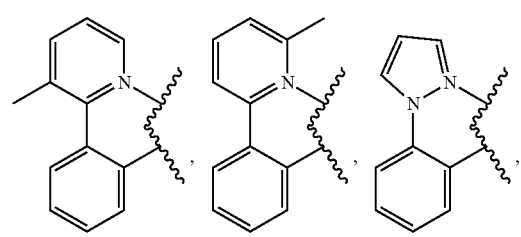
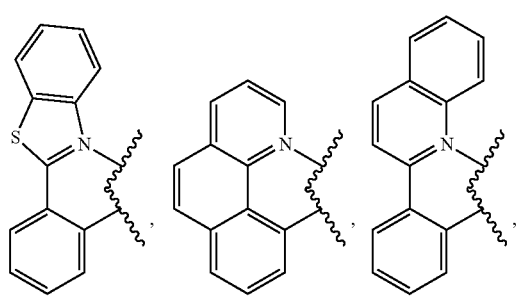
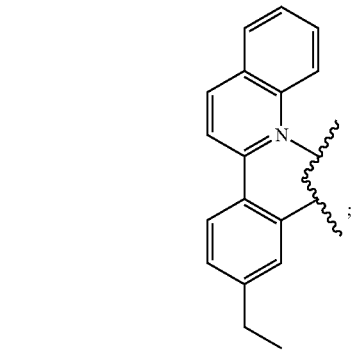
and
Ar³ is:
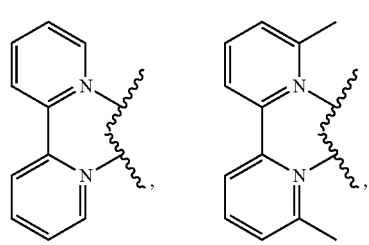
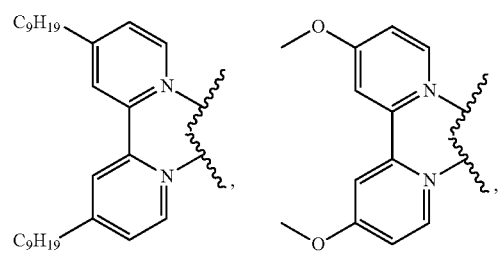
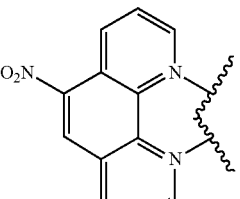
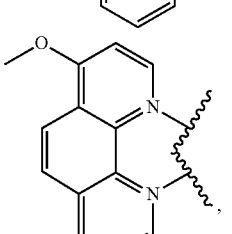
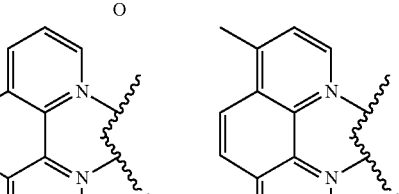
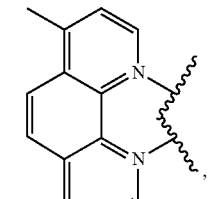
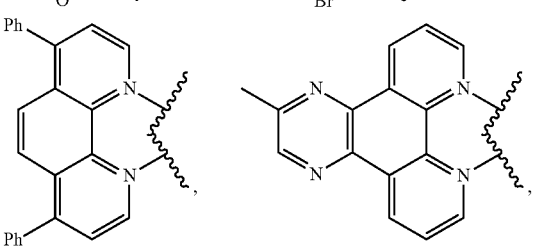

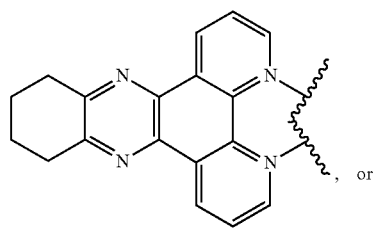
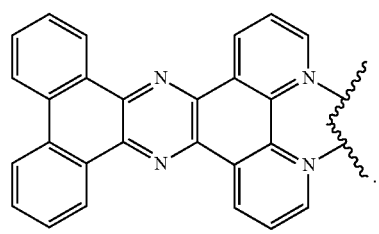
In certain embodiments, the metal complex is selected from the group consisting of:
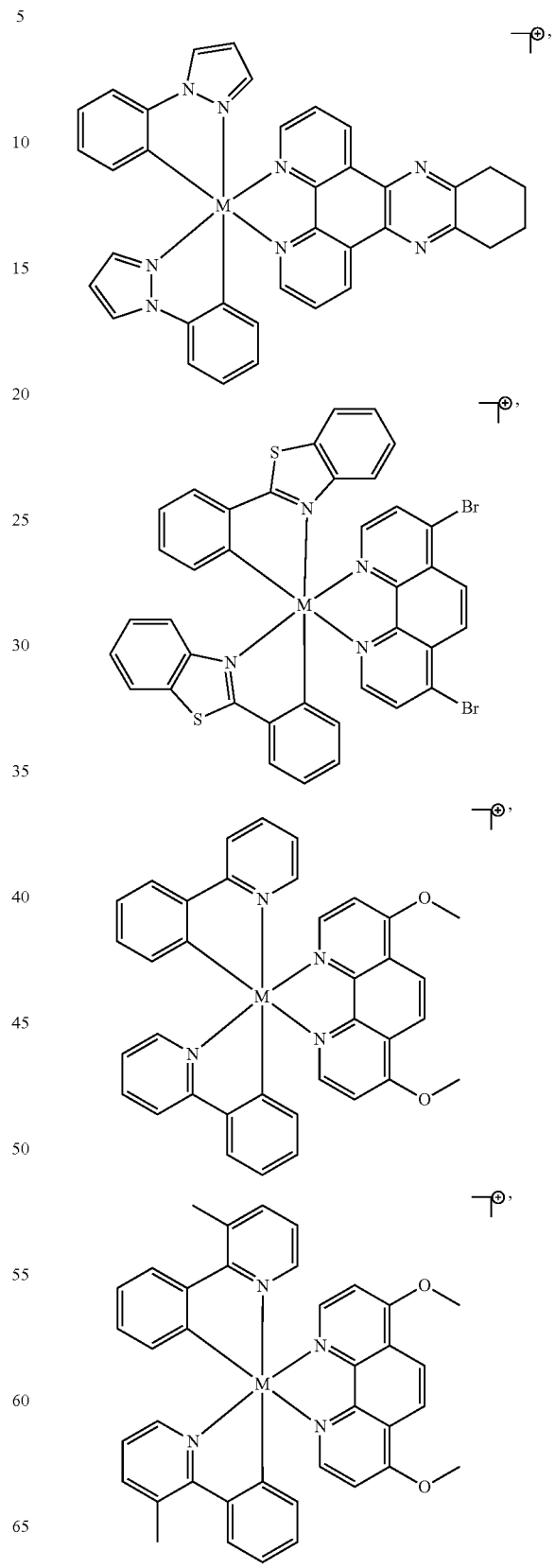

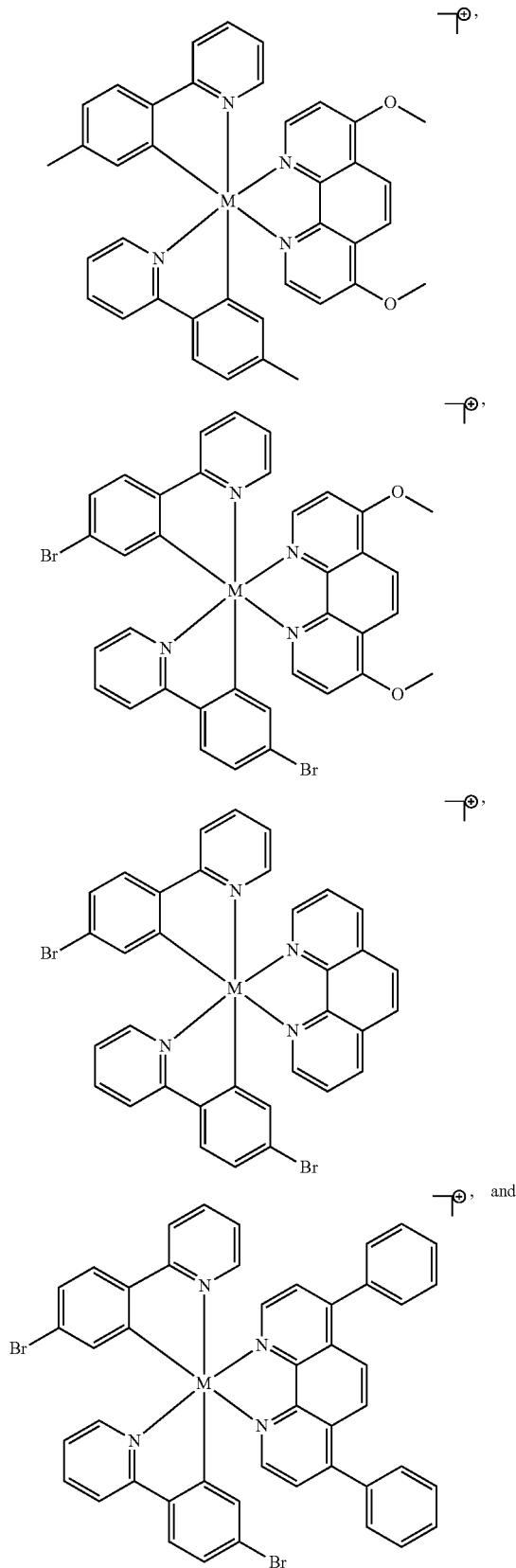

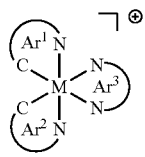

In a second aspect, provided herein is a method of promoting wound healing in a subject in need thereof, the method comprising: administering a therapeutically effective amount of a compound comprising a metal complex of Formula 1 and a pharmaceutically acceptable anion, wherein the metal complex of Formula 1 has the structure:

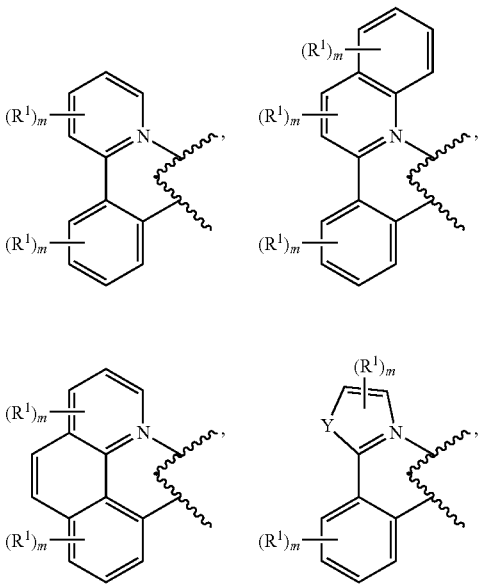

wherein M is Ir (III) or Rh (III);
each of $Ar^1$ and $Ar^2$ is independently selected from the group consisting of:

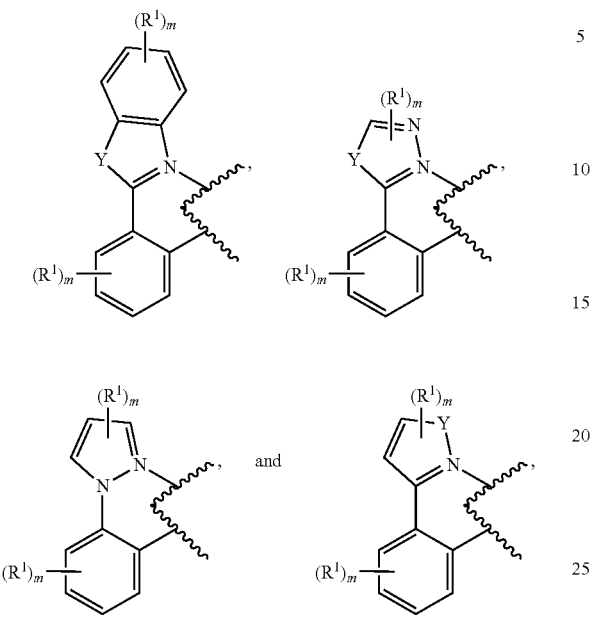

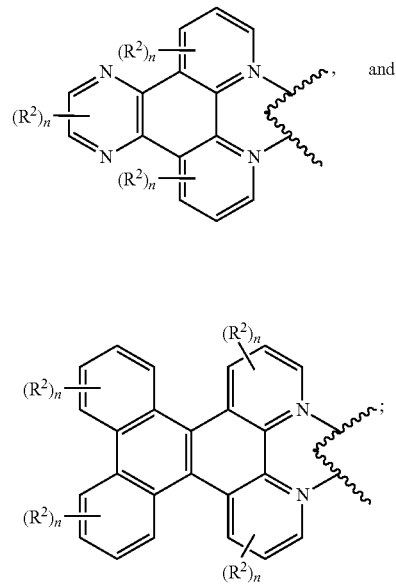

wherein m for each instance is independently a whole number selected from 0-2;

Y is S or O; and $R^1$ for each instance is independently selected from the group consisting of halide, nitro, nitrile, azido, —$OR^3$, —$OP(O)(OR^3)_2$, —$SR^3$, —$N(R^3)_2$, —$P(O)(OR^3)_2$, —$C(O)R^3$, —$C(O)OR^3$, —$OC(O)R^3$, —$N(R^3)C(O)R^3$, —$C(O)N(R^3)_2$, —$N(R^3)C(O)OR^3$, —$OC(O)N(R^3)$—, —$OC(O)OR^3$, —$N(R^3)C(O)N(R^3)_2$, —$S(O)_2R^3$, —$S(O)_2OR^3$, —$S(O)_2N(R^3)_2$, —$N(R^3)S(O)_2R^3$, alkyl, haloalkyl, perhaloalkyl, alkenyl, alkynyl, cycloalkyl, heterocycloalkyl, aryl, heteroaryl, aralkyl, and —$(CR^4{}_2)_pA$, wherein p for each instance is independently a whole number selected from 1-10; $R^4$ for each instance is hydrogen, alkyl, cycloalkyl, aryl, or heteroaryl; and A for each instance is independently halide, nitrile, nitro, azido, —$OR^3$, —$SR^3$, —$N(R^3)_2$, —$C(O)R^3$, —$C(O)OR^3$, —$OC(O)R^3$, —$N(R^3)C(O)R^3$, —$C(O)N(R^3)_2$, —$N(R^3)C(O)OR^3$, —$OC(O)N(R^3)$—, —$OC(O)OR^3$, —$N(R^3)C(O)N(R^3)_2$, —$S(O)_2R^3$, —$S(O)_2N(R^3)_2$, —$N(R^3)S(O)_2R^3$, alkynyl, heterocycloalkyl, aryl, heteroaryl, and aralkyl; or two instances of $R^1$ together with the carbons to which they are bonded form an optionally substituted 5-6 membered carbocycle;

$Ar^3$ is selected from the group consisting of:

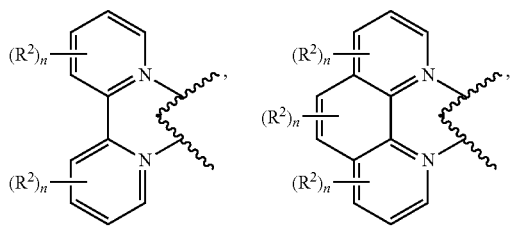

wherein n for each instance is independently a whole number selected from 0-2;

$R^2$ for each instance is independently selected from the group consisting of halide, nitro, nitrile, azido, —$OR^3$, —$OP(O)(OR^3)_2$, —$SR^3$, —$N(R^3)_2$, —$P(O)(OR^3)_2$, —$C(O)R^3$, —$C(O)OR^3$, —$OC(O)R^3$, —$N(R^3)C(O)R^3$, —$C(O)N(R^3)_2$, —$N(R^3)C(O)OR^3$, —$OC(O)N(R^3)$—, —$OC(O)OR^3$, —$N(R^3)C(O)N(R^3)_2$, —$S(O)_2R^3$, —$S(O)_2OR^3$, —$S(O)_2N(R^3)_2$, —$N(R^3)S(O)_2R^3$, alkyl, haloalkyl, perhaloalkyl, alkenyl, alkynyl, cycloalkyl, heterocycloalkyl, aryl, heteroaryl, aralkyl, and —$(CR^4{}_2)_pA$, wherein p for each instance is independently a whole number selected from 1-10; $R^4$ for each instance is selected from the group consisting of hydrogen, alkyl, cycloalkyl, aryl, and heteroaryl; or two instances of $R^4$ taken together with the carbon to which they are bonded form a 3-6 membered cycloalkyl; and A for each instance is independently selected from the group consisting of halide, nitrile, nitro, azido, —$OR^3$, —$SR^3$, —$N(R^3)_2$, —$C(O)R^3$, —$C(O)OR^3$, —$OC(O)R^3$, —$N(R^3)C(O)R^3$, —$C(O)N(R^3)_2$, —$N(R^3)C(O)OR^3$, —$OC(O)N(R^3)$—, —$OC(O)OR^3$, —$N(R^3)C(O)N(R^3)_2$, —$S(O)_2R^3$, —$S(O)_2N(R^3)_2$, —$N(R^3)S(O)_2R^3$, alkynyl, heterocycloalkyl, aryl, heteroaryl, and aralkyl; or two instances of $R^2$ together with the carbons to which they are bonded form an optionally substituted 5-6 membered carbocycle; and $R^3$ for each instance is independently hydrogen, alkyl, haloalkyl, perhaloalkyl, alkenyl, alkynyl, cycloalkyl, heterocycloalkyl, aryl, heteroaryl, or aralkyl; or two instances of $R^3$ together with the atoms to which they are bonded form a 3-6 membered cycloalkyl or heterocycloalkyl.

In certain embodiments, each of $Ar^1$ and $Ar^2$ is independently selected from the group consisting of:

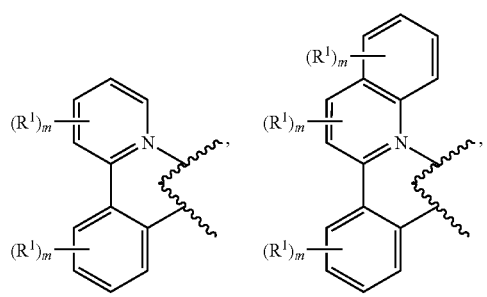

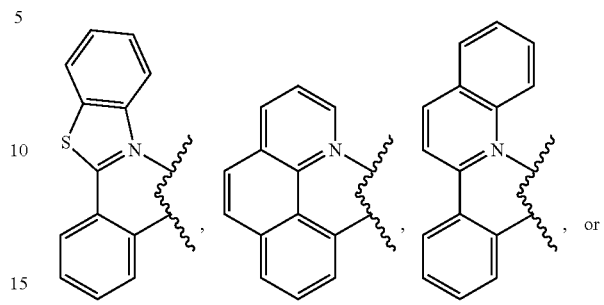

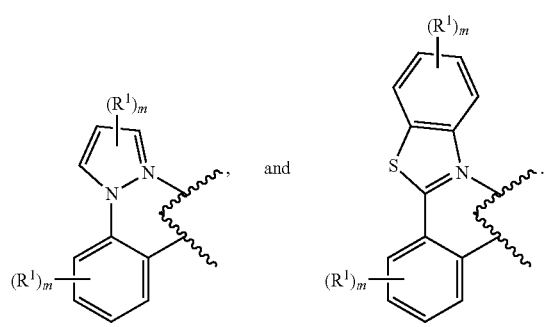

In certain embodiments, each instance of $R^1$ is independently selected from the group consisting of alkyl, halide, and —$OR^3$.

In certain embodiments, each of $Ar^1$ and $Ar^2$ is:

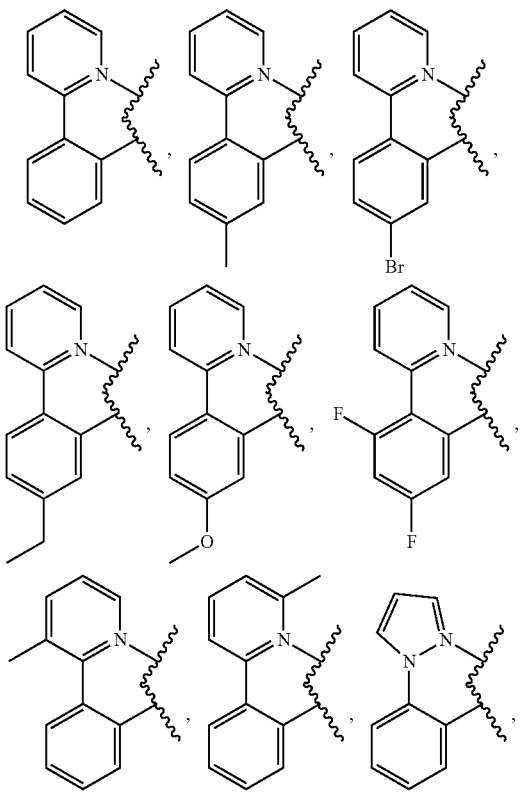

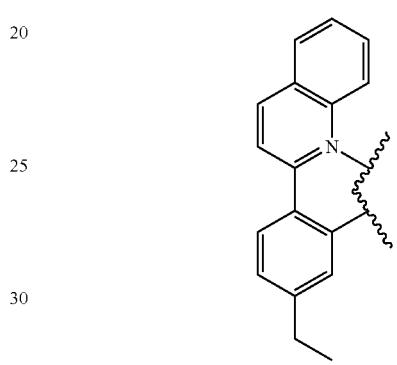

In certain embodiments, each instance of $R^2$ is independently selected from the group consisting of alkyl, aryl, halide, nitro, —$OR^3$, —$P(O)(OR^3)_2$, and —$C(O)OR^3$; or two instances of $R^2$ taken together with the carbon to which they are bonded form a 6 membered cycloalkyl.

In certain embodiments, $Ar^3$ is selected from the group consisting of:

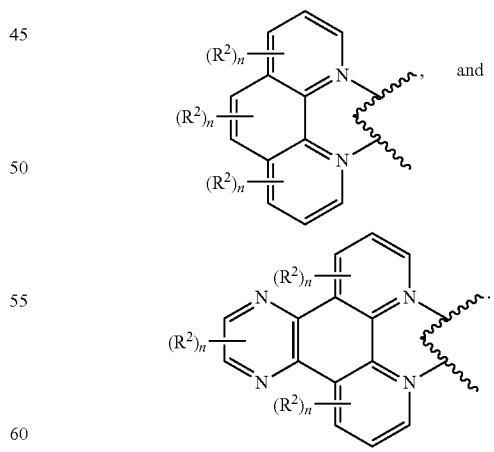

In certain embodiments, each instance of $R^2$ is independently selected from the group consisting of alkyl, halide, phenyl, and —$OR^3$; or two instances of $R^2$ taken together with the carbon to which they are bonded form a 6 membered cycloalkyl.

In certain embodiments, Ar³ is:
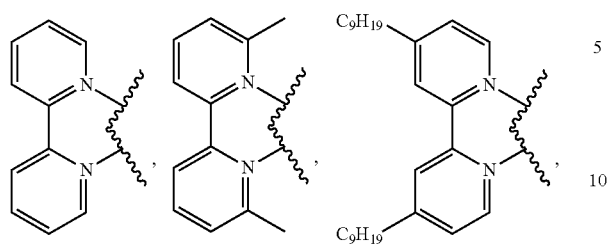
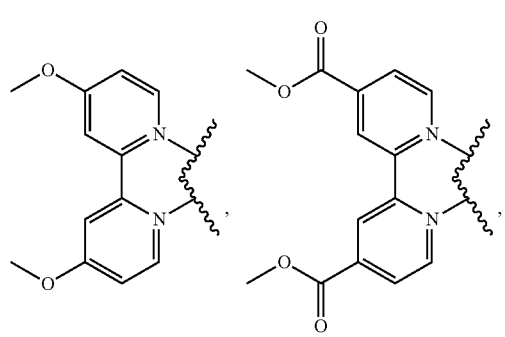
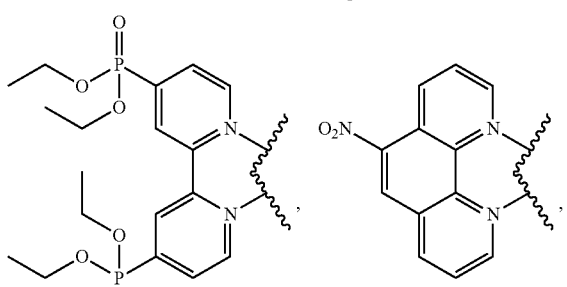
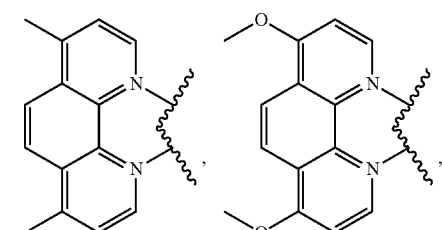
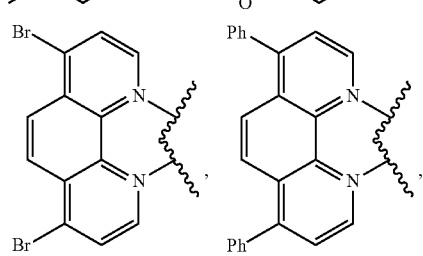
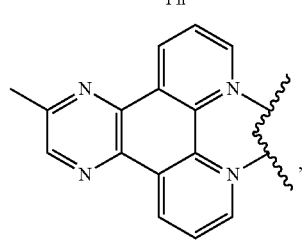
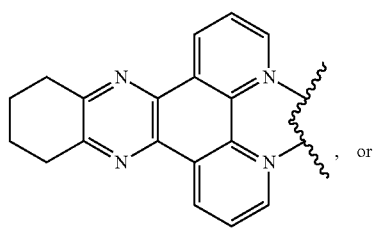
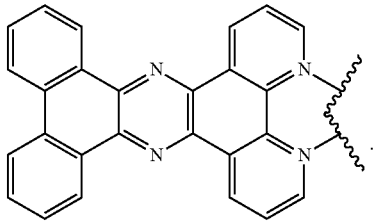
In certain embodiments, each of Ar¹ and Ar² is:
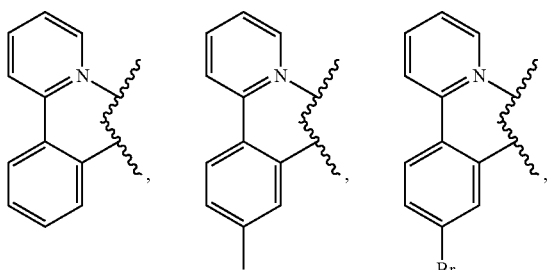
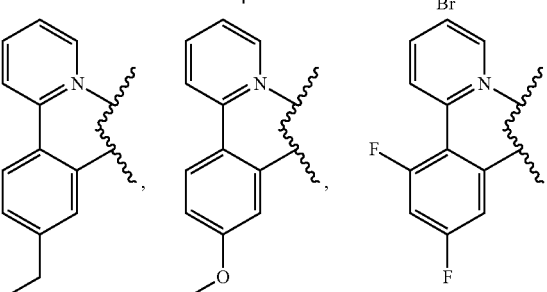
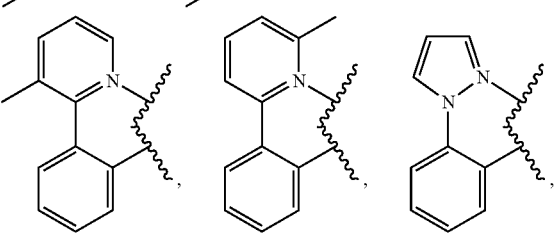
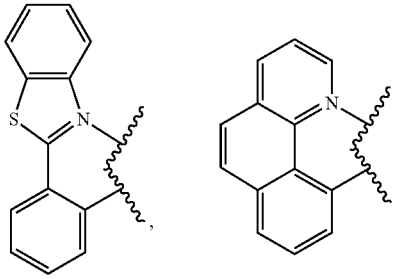

-continued
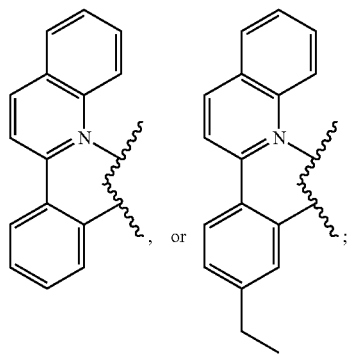, or ;
and
Ar³ is:
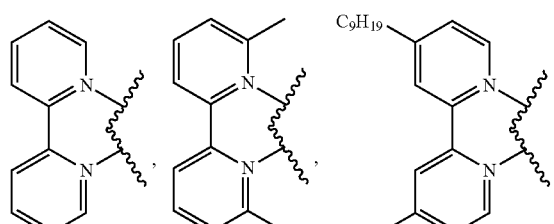
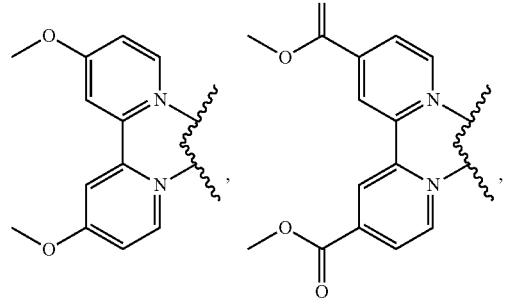
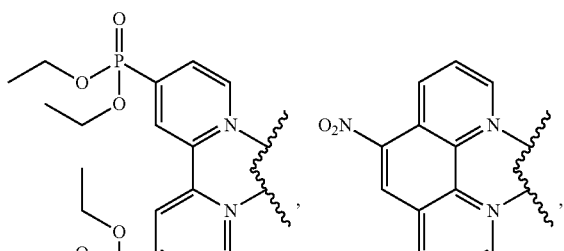
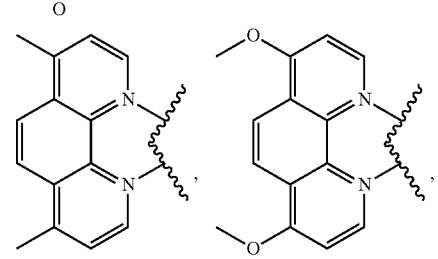
-continued
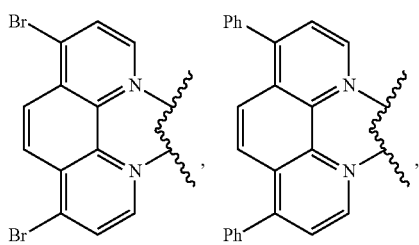
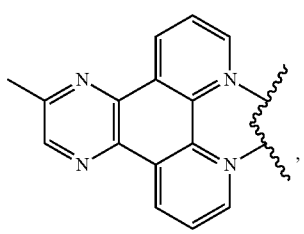
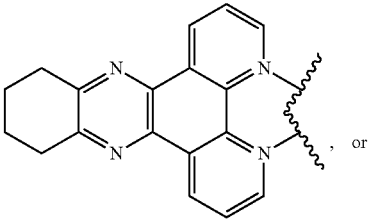,  or
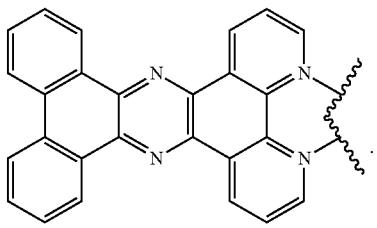.
In certain embodiments, the metal complex is selected from the group consisting of:
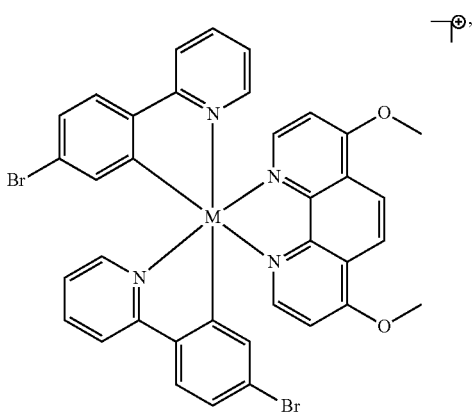

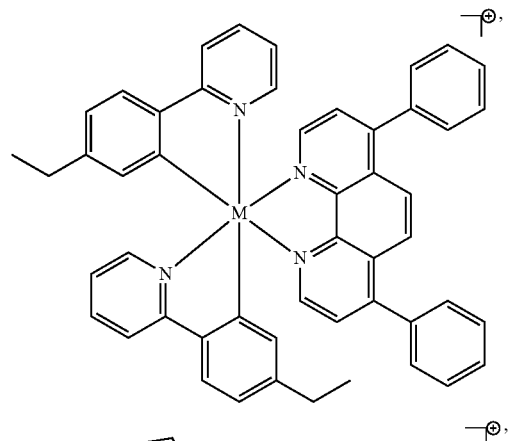
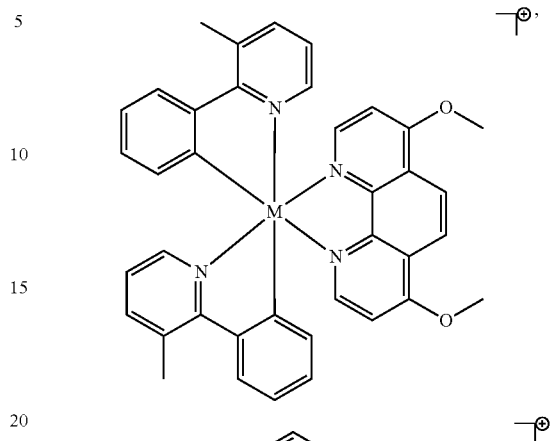
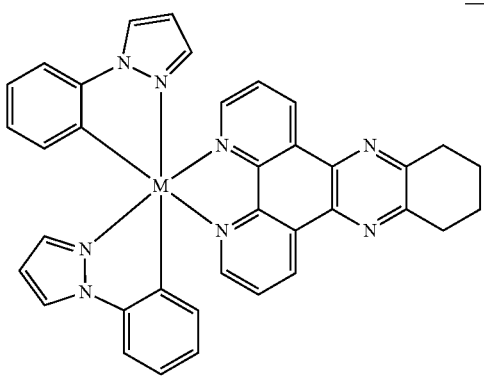
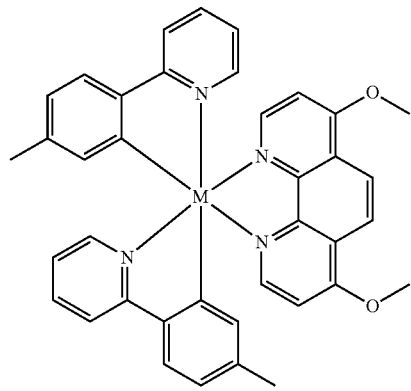
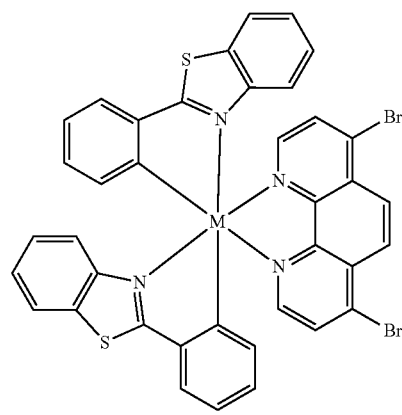
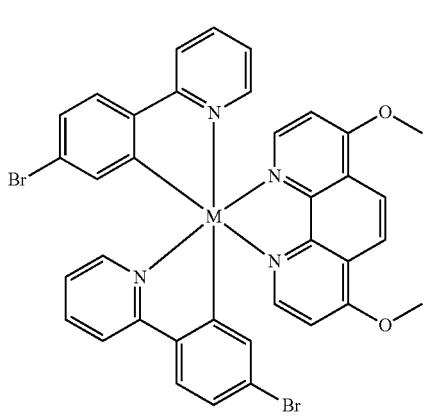
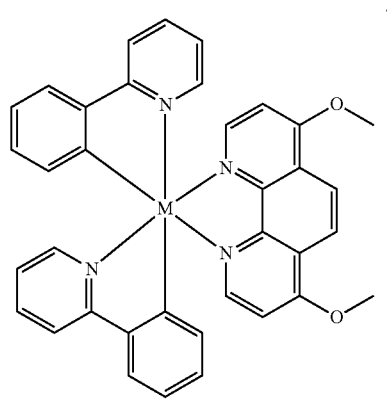
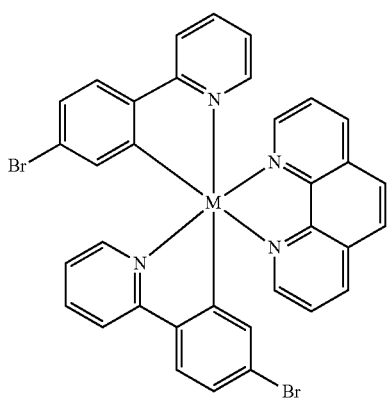

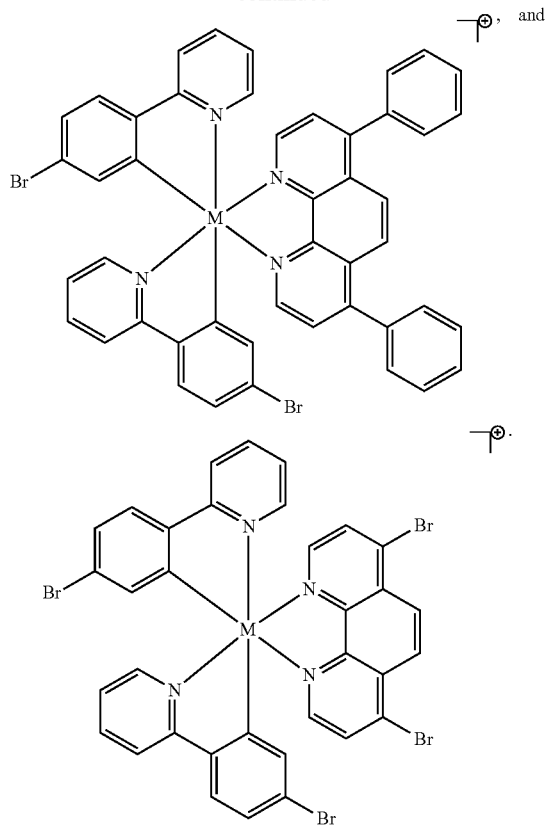

BRIEF DESCRIPTION OF THE DRAWINGS

The above and other objects and features of the present disclosure will become apparent from the following description of the disclosure, when taken in conjunction with the accompanying drawings.

DETAILED DESCRIPTION

Definitions

Figure 1:
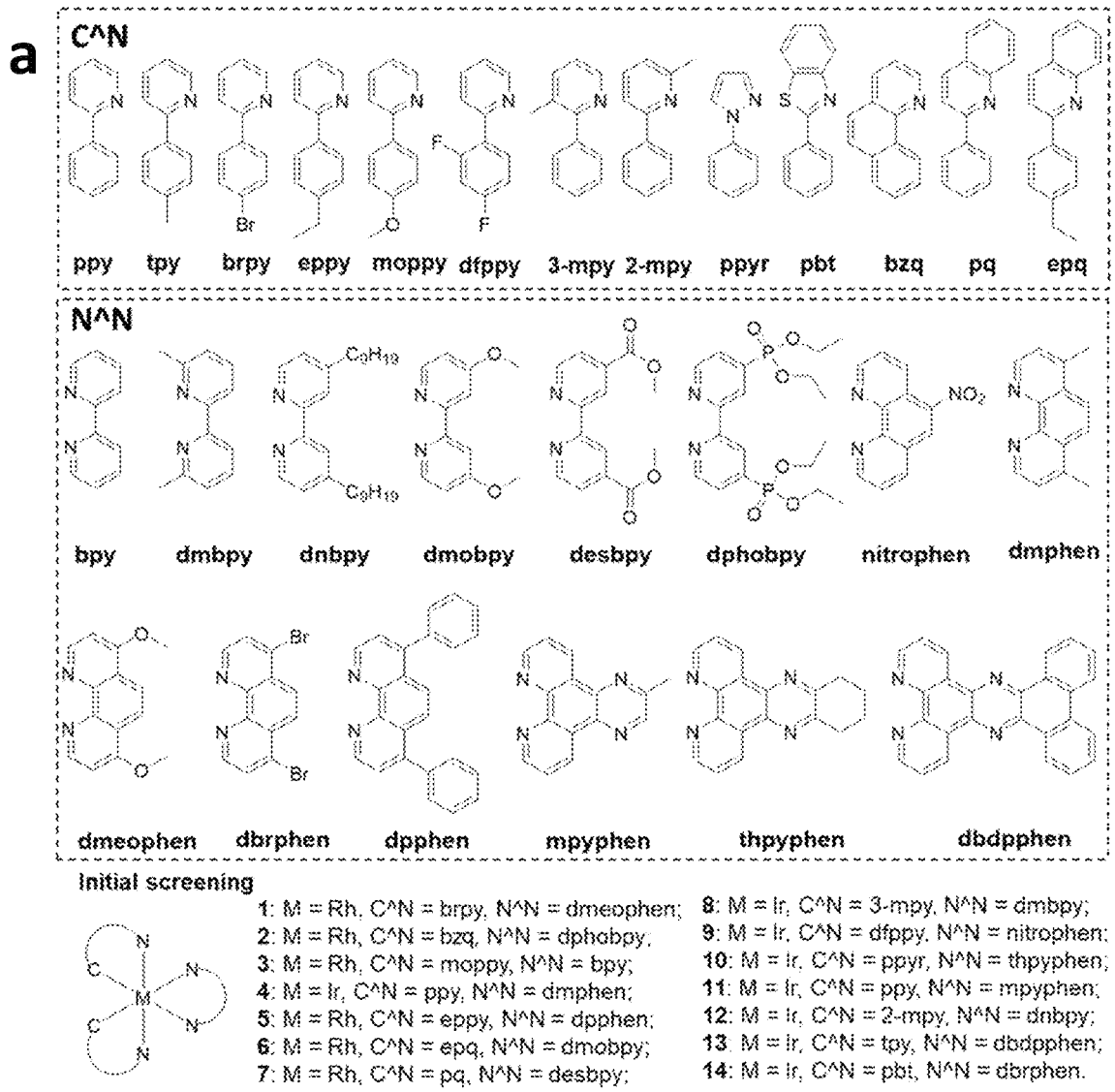
FIG. 1 depicts the effect of complexes on HIF-1α activation of the HRE-driven reporter as determined via a dual luciferase reporter assay. (A) Chemical structures of the small molecules used for preliminary screening. All complexes are as racemic $PF_6^-$ salts. (B) Effect of complexes 1-14 on HIF-1α activation of the HRE-driven reporter. HEK293 cells were treated with complexes 1-14 or P1 for 8 h. Error bars represent the standard deviations (SD) of the results from three independent experiments. P values were calculated using a two-sided t-test. *P<0.05, **P<0.01 vs. DMSO group. (C) Chemical structures of the focused library of cyclometallated Ir(III) and Rh(III) complexes. (D) Effect of complexes 1a-1n on HIF-1α activation of the HRE-driven reporter. HEK293 cells were treated with complexes 1a-1n or P1 for 8 h. (E) Dose-dependent effect of complex 1a on HIF-1α-driven activity. HEK293 cells were treated with the indicated concentrations of complex 1a for 8 h. Data are expressed as means±SD (n=3 independent experiments), P values were calculated using a two-sided t-test. #P<0.05 1a vs. P1, NS (not significant, P>0.05) 1 vs. P1. *P<0.05, **P<0.01 vs. DMSO group. (F) Schematic diagram of the DLR showing co-transfected HRE-luciferase and pRL-TK plasmids in HEK293 cells. Data are expressed as means±SD (n=3 independent experiments).
Figure 1:
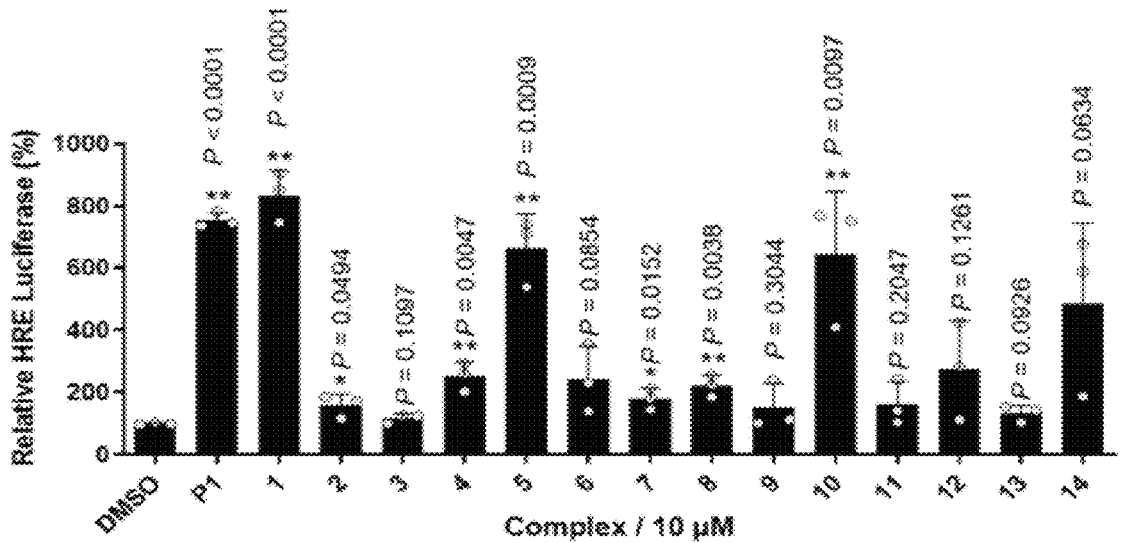
Figure 1:
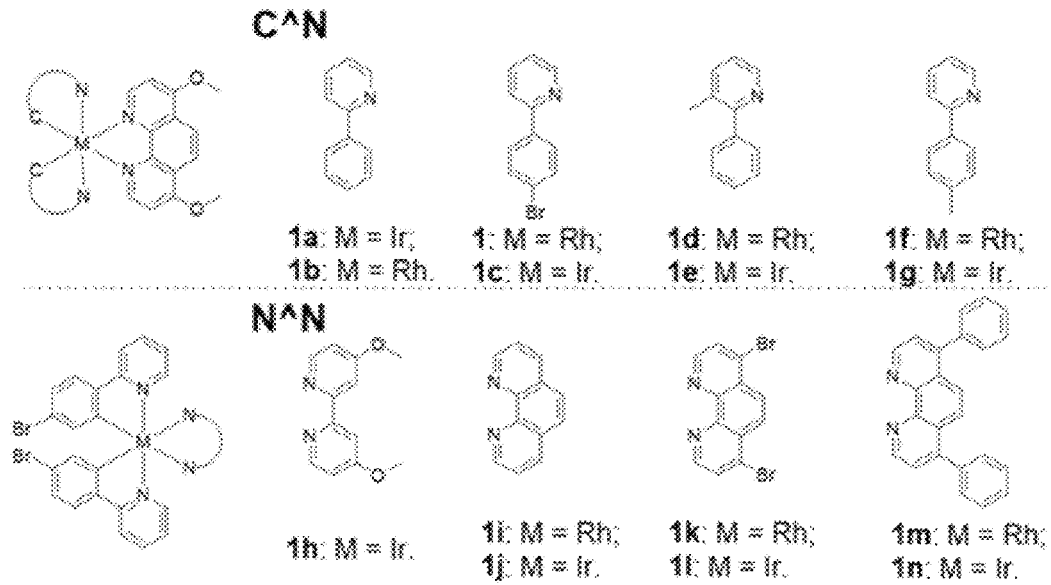
Figure 1:
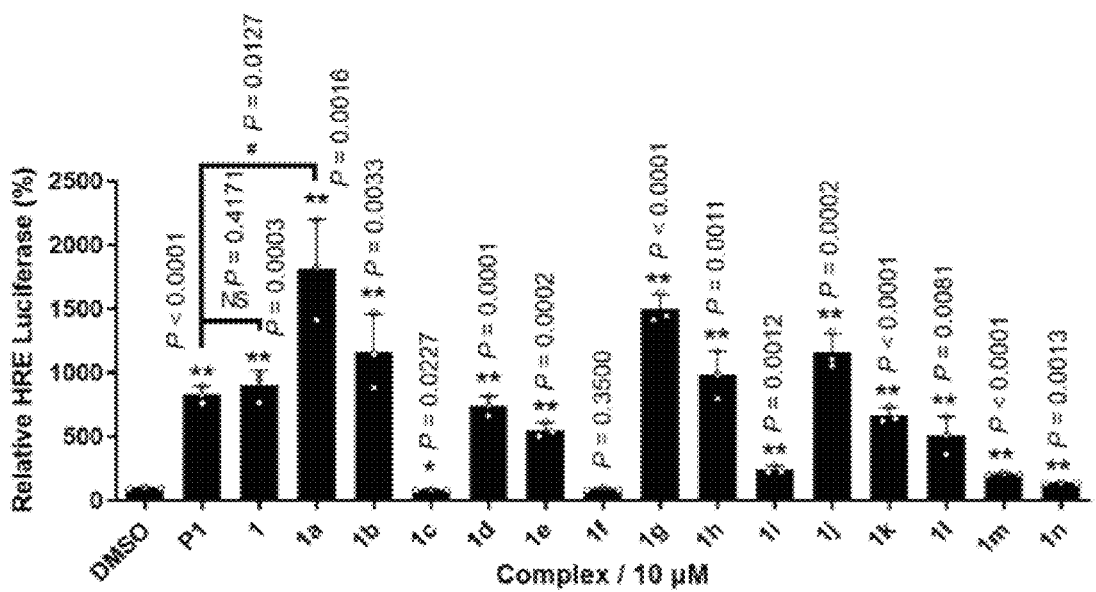
Figure 1:
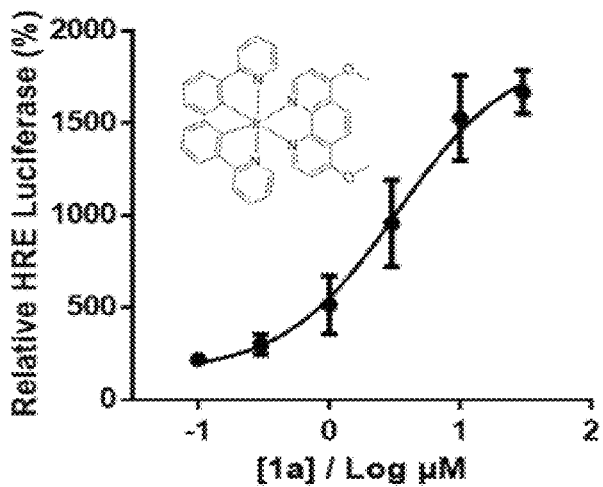
Figure 1:
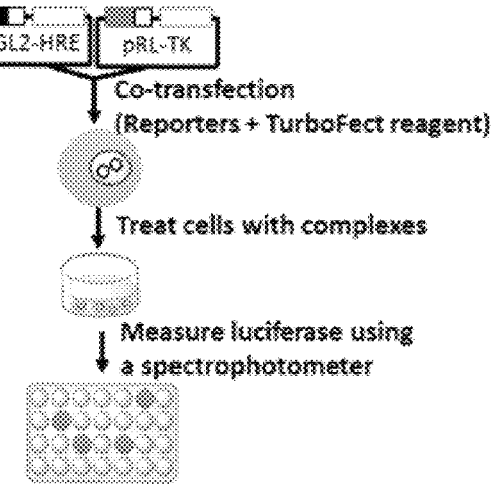

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±9%, ±7%, ±6%, ±5%, ±4%, ±3%, ±2%, ±1%, ±0.75%, ±0.5%, ±0.25%, ±0.2%, ±0.1%, or ±0% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, "halo", "halide", or "halogen" refers to fluoro, chloro, bromo, and iodo.

As used herein, "alkyl" refers to a straight-chain or branched saturated hydrocarbon group. Examples of alkyl groups include methyl-, ethyl-, propyl (e.g., n-propyl and isopropyl), butyl (e.g., n-butyl, iso-butyl, sec-butyl, tert-butyl), pentyl groups (e.g., 1-methylbutyl, 2-methylbutyl, iso-pentyl, tert-pentyl, 1,2-dimethylpropyl, neopentyl, and 1-ethylpropyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In certain embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In certain embodiments, alkyl groups can be optionally substituted as described herein. An alkyl group is generally not substituted with another alkyl group, an alkenyl group, or an alkynyl group.

The term "aralkyl" is art-recognized and refers to an alkyl group substituted with an aryl group (e.g., an aromatic or heteroaromatic group).

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be optionally substituted as described herein. The aryl ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., ~$C_6F_5$), are included within the definition of "haloaryl." In certain embodiments, an aryl group is substituted with another aryl group and can be referred to as a biaryl group. Each of the aryl groups in the biaryl group can be optionally substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be optionally substituted as described herein. The heterocyclic ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl, aryl, heteroaryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like.

"Enantiomers" are a pair of stereoisomers that are non-superimposable mirror images of each other. A mixture of a pair of enantiomers in equal proportions can be known as a "racemic" mixture. The term "(+/−)" is used to designate a racemic mixture where appropriate. The absolute stereochemistry can be specified according to the Cahn-Ingold-Prelog R-S system. When a compound is an enantiomer, the stereochemistry at each chiral carbon and/or axis of chirality can be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein can contain one or more asymmetric centers and/or axis of chirality and can thus give rise to enantiomers, diastereomers, and other stereoisomeric forms that can be defined, in terms of absolute stereochemistry at each asymmetric atom or axis of chirality, as (R)- or (S)—. The present compounds and methods are meant to include all such possible isomers, including substantially enantiopure forms and intermediate mixtures. Optically active (R)- and (S)-isomers can be prepared, for example, using chiral synthons or chiral reagents, or resolved using conventional techniques.

The representation "⁇" as used herein in connection to chemical a group or moiety is intended to represent the covalent bond that the aforementioned chemical group or moiety is covalently bonded to another chemical group, moiety, or atom.

As used herein by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "therapeutically effective" means the amount of the composition used is of sufficient quantity to ameliorate one or more causes or symptoms of a disease or disorder. Such amelioration only requires a reduction or alteration, not necessarily elimination.

As used herein, the term pharmaceutically acceptable salt refers to any salt of the compound of this invention which retains its biological properties and which is not toxic or otherwise undesirable for pharmaceutical use. Such salts may be derived from a variety of organic and inorganic counterions well known in the art and include them. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo [2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion (e.g., an alkali metal ion, an alkaline earth ion or an aluminum ion), or alkali metal or alkaline earth metal hydroxides (e.g., sodium, potassium, calcium, magnesium, aluminum, lithium, zinc, and barium hydroxide), ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. In addition, examples of salts include sodium, potassium, calcium, magnesium, ammonium, tetraalkylammonium and the like, and when the compound contains a basic functionality, salts of non-toxic organic or inorganic acids, such as halides (e.g., chloride, bromide, and iodide), sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate; fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

When trade names are used herein, applicants intend to independently include the trade name product formulation, the generic drug, and the active pharmaceutical ingredient(s) of the trade name product.

The present disclosure provides a method of inhibiting a protein-protein interaction between VHL tumor-suppressor protein and HIF-1α in a subject in need thereof, the method comprising: administering a therapeutically effective amount of a compound comprising a metal complex of Formula 1 and a pharmaceutically acceptable anion. In certain embodiments, the subject does not have cancer.

In certain embodiments, the subject has an angiogenesis-related disease, such as an ocular disease (e.g., age-related macular degeneration, diabetic retinopathy, or glaucoma), a cardiovascular disease (e.g., restenosis or atherosclerosis), a skin disease (e.g., psoriasis) arthritis (e.g., rheumatoid arthritis), inflammation, endometriosis, and hemangioma. In certain embodiments, the angiogenesis-related disease is not cancer.

The pharmaceutically acceptable salt may comprise any counterion that has been previously used in an FDA-approved drug and/or are generally recognized as safe (GRAS). In certain embodiments, the pharmaceutically anion is selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, acetate, succinate, sulfate, tartrate, teoclate, and tosylate, and the like.

The metal complex of Formula 1 can have the structure:

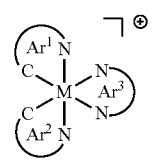

wherein M is Ir (III) or Rh (III);
each of $Ar^1$ and $Ar^2$ is independently selected from the group consisting of:

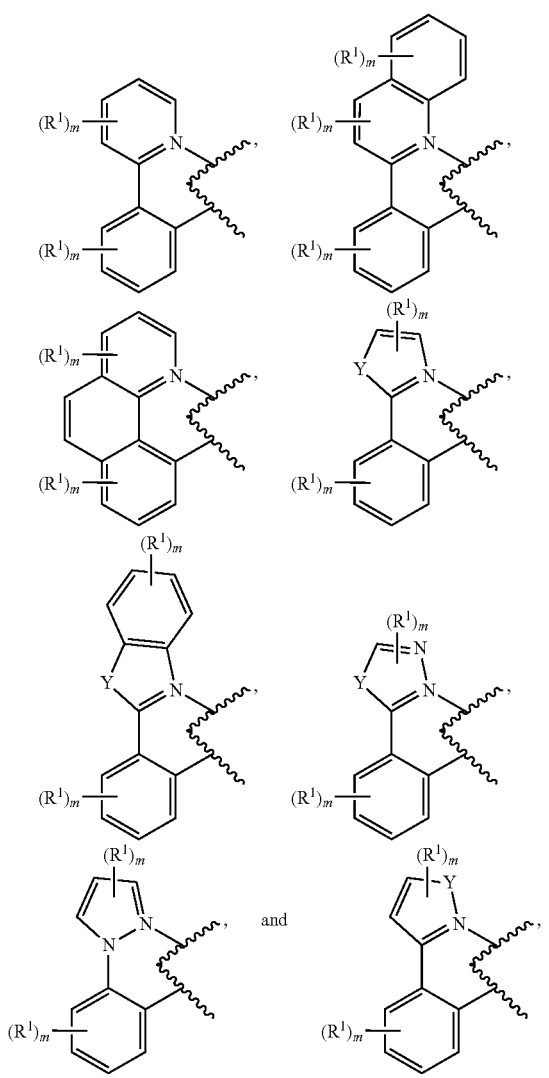

wherein m for each instance is independently a whole number selected from 0-2;
Y is S or O; and
R¹ for each instance is independently selected from the group consisting of halide, nitro, nitrile, azido, —OR³, —OP(O)(OR³)$_2$, —SR³, —N(R³)$_2$, —P(O)(OR³)$_2$, —C(O)R³, —C(O)OR³, —OC(O)R³, —N(R³)C(O)R³, —C(O)N(R³)$_2$, —N(R³)C(O)OR³, —OC(O)N(R³)—, —OC(O)OR³, —N(R³)C(O)N(R³)$_2$, —S(O)$_2$R³, —S(O)$_2$OR³, —S(O)$_2$N(R³)$_2$, —N(R³)S(O)$_2$R³, alkyl, haloalkyl, perhaloalkyl, alkenyl, alkynyl, cycloalkyl, heterocycloalkyl, aryl, heteroaryl, aralkyl, and —(CR⁴$_2$)$_p$A, wherein p for each instance is independently a whole number selected from 1-10; R⁴ for each instance is hydrogen, alkyl, cycloalkyl, aryl, or heteroaryl; and A for each instance is independently halide, nitrile, nitro, azido, —OR³, —SR³, —N(R³)$_2$, —C(O)R³, —C(O)OR³, —OC(O)R³, —N(R³)C(O)R³, —C(O)N(R³)$_2$, —N(R³)C(O)OR³, —OC(O)N(R³)—, —OC(O)OR³, —N(R³)C(O)N(R³)$_2$, —S(O)$_2$R³, —S(O)$_2$N(R³)$_2$, —N(R³)S(O)$_2$R³, alkynyl, heterocycloalkyl, aryl, heteroaryl, and aralkyl; or two instances of R¹ together with the carbons to which they are bonded form an optionally substituted 5-6 membered carbocycle;

Ar³ is selected from the group consisting of:

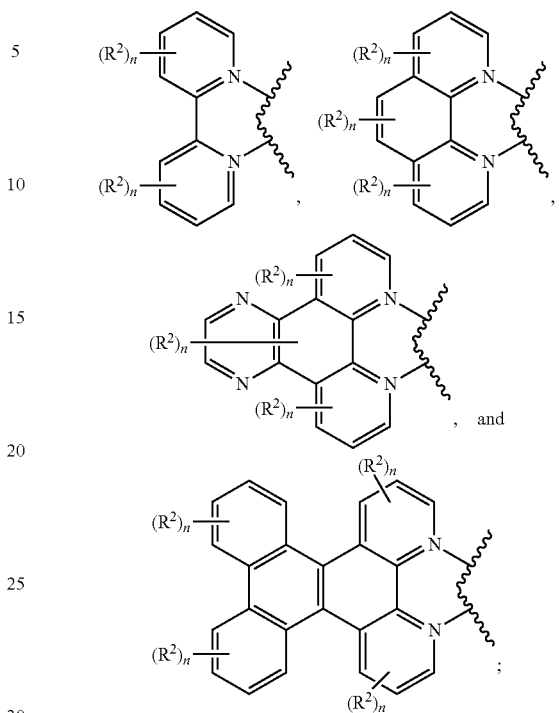

wherein n for each instance is independently a whole number selected from 0-2;
R² for each instance is independently selected from the group consisting of halide, nitro, nitrile, azido, —OR³, —OP(O)(OR³)$_2$, —SR³, —N(R³)$_2$, —P(O)(OR³)$_2$, —C(O)R³, —C(O)OR³, —OC(O)R³, —N(R³)C(O)R³, —C(O)N(R³)$_2$, —N(R³)C(O)OR³, —OC(O)N(R³)—, —OC(O)OR³, —N(R³)C(O)N(R³)$_2$, —S(O)$_2$R³, —S(O)$_2$OR³, —S(O)$_2$N(R³)$_2$, —N(R³)S(O)$_2$R³, alkyl, haloalkyl, perhaloalkyl, alkenyl, alkynyl, cycloalkyl, heterocycloalkyl, aryl, heteroaryl, aralkyl, and —(CR⁴$_2$)$_p$A, wherein p for each instance is independently a whole number selected from 1-10; R⁴ for each instance is selected from the group consisting of hydrogen, alkyl, cycloalkyl, aryl, and heteroaryl; or two instances of R⁴ taken together with the carbon to which they are bonded form a 3-6 membered cycloalkyl; and A for each instance is independently selected from the group consisting of halide, nitrile, nitro, azido, —OR³, —SR³, —N(R³)$_2$, —C(O)R³, —C(O)OR³, —OC(O) R³, —N(R³)C(O)R³, —C(O)N(R³)$_2$, —N(R³)C(O) OR³, —OC(O)N(R³)—, —OC(O)OR³, —N(R³)C(O) N(R³)$_2$, —S(O)$_2$R³, —S(O)$_2$N(R³)$_2$, —N(R³)S(O)$_2$R³, alkynyl, heterocycloalkyl, aryl, heteroaryl, and aralkyl; or two instances of R² together with the carbons to which they are bonded form an optionally substituted 5-6 membered carbocycle; and
R³ for each instance is independently hydrogen, alkyl, haloalkyl, perhaloalkyl, alkenyl, alkynyl, cycloalkyl, heterocycloalkyl, aryl, heteroaryl, or aralkyl; or two instances of R³ together with the atoms to which they are bonded form a 3-6 membered cycloalkyl or heterocycloalkyl.

The compound comprising the metal complex of Formula 1 must be charged balanced. The ratio of the metal complex of Formula 1 and the pharmaceutically acceptable anion can be represented by the formula $(A^{t+})_U(B^{u-})_T$ wherein A represents the metal complex of Formula 1, B represents the pharmaceutically acceptable anion, t represents the charge of the metal complex of Formula 1, u represents the charge of the pharmaceutically acceptable anion, U is equal to the absolute value of the charge of the pharmaceutically acceptable anion and T is equal to the absolute value of the charge of the metal complex of Formula 1. For example, when metal complex of Formula 1 has a charge of 1+ and the anion is $SO_4^{2-}$, which has a charge of −2, the charged balance formula would be $(A^{3+})_2(SO_4^{2-})$.

The metal complex of Formula 1 can comprise the bidentate ligands, $Ar^1$, $Ar^2$, and $Ar^3$, coordinated to the octahedral metal center at equatorial-equatorial positions, equatorial-axial positions, and combinations thereof. The present disclosure contemplates all such isomers as well as stereoisomers of the metal complexes described herein. In certain embodiments, two bidentate ligands occupy equatorial-axial positions and one bidentate ligand occupies an equatorial-equatorial position.

$R^1$ for each instance can independently be selected from the group consisting of halide, nitro, nitrile, azido, —$OR^3$, —$OP(O)(OR^3)_2$, —$N(R^3)_2$, —$P(O)(OR^3)_2$, —$C(O)OR^3$, —$OC(O)R^3$, —$N(R^3)C(O)R^3$, —$C(O)N(R^3)_2$, —$N(R^3)C(O)OR^3$, —$OC(O)N(R^3)$—, —$N(R^3)C(O)N(R^3)_2$, —$S(O)_2R^3$, —$S(O)_2N(R^3)_2$, —$N(R^3)S(O)_2R^3$, alkyl, haloalkyl, perhaloalkyl, cycloalkyl, heterocycloalkyl, aryl, heteroaryl, aralkyl, and —$(CR^4{}_2)_pA$. In certain embodiments, $R^1$ for each instance can independently be selected from the group consisting of $C_1$-$C_6$ alkyl, such as methyl, ethyl, n-propyl, and isopropyl, halide, such as fluoride, chloride, bromide, and iodide, and —$OR^3$, wherein $R^3$ is $C_1$-$C_6$ alkyl, $C_1$-$C_3$ alkyl, and $C_1$-$C_2$ alkyl.

In instances in which two $R^1$ together with the carbons to which they are bonded form an optionally substituted 5-6 membered carbocycle, the 5-6 membered can be formed from two vicinal $R^1$ (i.e., each bonded to adjacent carbon atoms) to form a fused carbocycle selected from the group consisting of a fused cyclopentane, a fused cyclohexane, and a fused phenyl each of which can be optionally substituted with 1 or 2 $R^1$.

$R^2$ for each instance can independently be selected from the group consisting of halide, nitro, nitrile, azido, —$OR^3$, —$OP(O)(OR^3)_2$, —$N(R^3)_2$, —$P(O)(OR^3)_2$, —$C(O)OR^3$, —$OC(O)R^3$, —$N(R^3)C(O)R^3$, —$C(O)N(R^3)_2$, —$N(R^3)C(O)OR^3$, —$OC(O)N(R^3)$—, —$N(R^3)C(O)N(R^3)_2$, —$S(O)_2R^3$, —$S(O)_2N(R^3)_2$, —$N(R^3)S(O)_2R^3$, alkyl, haloalkyl, perhaloalkyl, cycloalkyl, heterocycloalkyl, aryl, heteroaryl, aralkyl, and —$(CR^4{}_2)_pA$. In certain embodiments, $R^2$ is independently selected from the group consisting of $C_1$-$C_6$ alkyl, such as methyl, ethyl, n-propyl, and isopropyl, halide, such as fluoride, chloride, bromide, and iodide, nitro, and —$OR^3$, optionally substituted phenyl, —$P(O)(OR^3)_2$, and —$C(O)OR^3$, wherein $R^3$ is $C_1$-$C_6$ alkyl, $C_1$-$C_3$ alkyl, and $C_1$-$C_2$ alkyl.

In instances in which two $R^2$ together with the carbons to which they are bonded form an optionally substituted 5-6 membered carbocycle, the 5-6 membered can be formed from two vicinal $R^2$ (i.e., each bonded to adjacent carbon atoms) to form a fused carbocycle selected from the group consisting of a fused cyclopentane, a fused cyclohexane, and a fused phenyl each of which can be optionally substituted with 1 or 2 $R^2$. In certain exemplary embodiments, in which two $R^2$ together with the carbons to which they are bonded form an optionally substituted 5-6 membered carbocycle, $Ar^2$ has the structure:

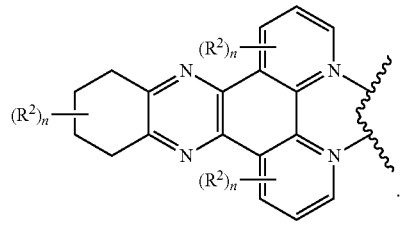

$R^4$ for each instance can independently be selected from the group consisting of hydrogen, $C_1$-$C_6$ alkyl, $C_1$-$C_3$ alkyl, $C_1$-$C_2$ alkyl, $C_3$-$C_6$ cycloalkyl, and optionally substituted phenyl. In certain embodiments, $R^4$ for each instance can independently be selected from the group consisting of hydrogen and methyl.

In certain embodiments, the metal complex is selected from the group consisting of:

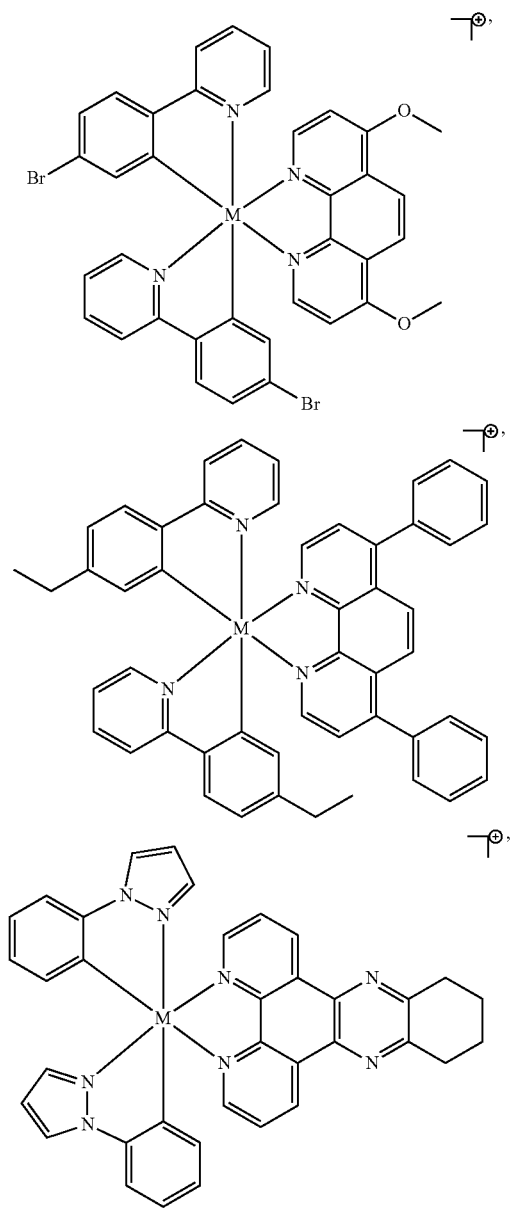

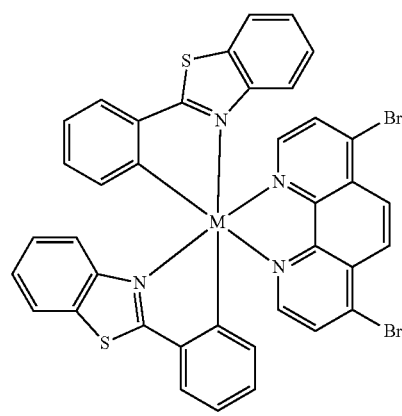
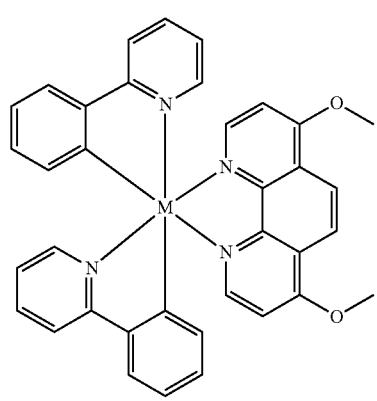
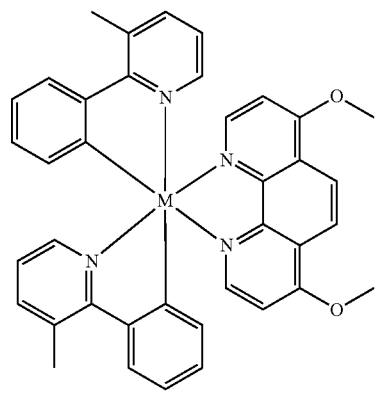
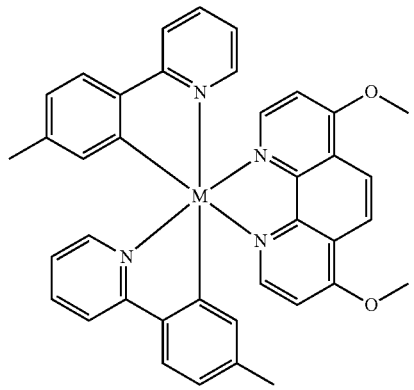
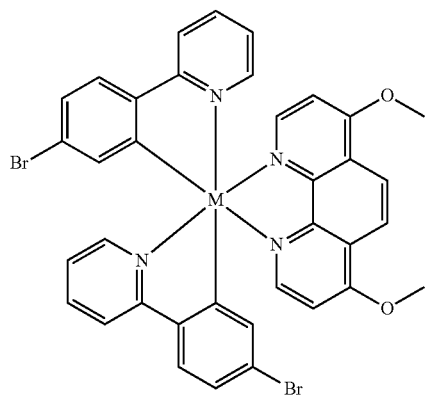
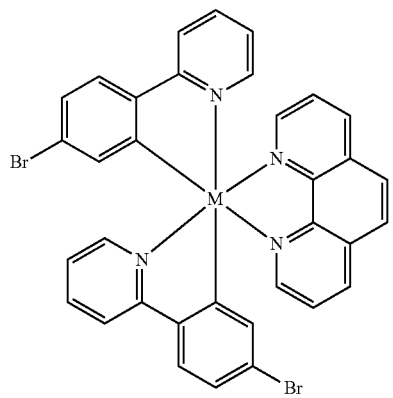
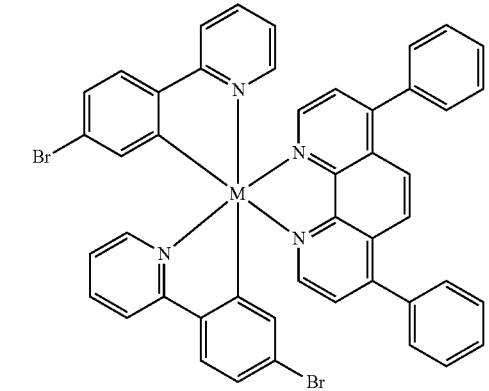
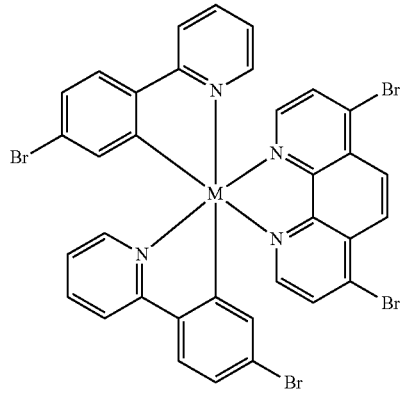
Also provided herein is a method of promoting would healing in a subject in need thereof, the method comprising:

administering a therapeutically effective amount of a compound comprising a metal complex of Formula 1 and a pharmaceutically acceptable anion, wherein the metal complex of Formula 1.

The present disclosure also provides a compound comprising a metal complex and a pharmaceutically acceptable anion, wherein the metal complex has the structure:

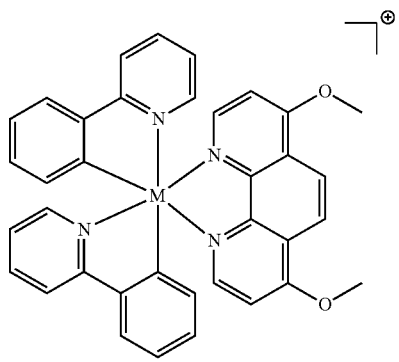

wherein M is Rh(III) or Ir(III).

The present disclosure also provides a pharmaceutical composition comprising any one of the compounds described herein and at least one pharmaceutically acceptable excipient.

The compounds described herein and their pharmaceutically acceptable salts can be administered to a subject either alone or in combination with pharmaceutically acceptable carriers or diluents in a pharmaceutical composition according to standard pharmaceutical practice. The compounds can be administered orally or parenterally. Parenteral administration includes intravenous, intramuscular, intraperitoneal, subcutaneous and topical, the preferred method being intravenous administration or topical administration.

Accordingly, the present disclosure provides pharmaceutically acceptable compositions, which comprise a therapeutically-effective amount of one or more of the compounds described herein, formulated together with one or more pharmaceutically acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) topical, for example, ointments, creams, sterile solution, or suspension.

As set out herein, certain embodiments of the compounds described herein may contain a basic functional group, such as amino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present disclosure. These salts can be prepared in situ in the administration vehicle or the dosage form manufacturing process, or by separately reacting a purified polypeptide conjugate of the invention in its free base form with a suitable organic or inorganic acid, and isolating the salt thus formed during subsequent purification. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the compounds of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising the compounds include the step of bringing into association a polypeptide conjugate described herein with the carrier and, optionally, one or more accessory ingredients. In general, the formulations are prepared by uniformly and intimately bringing into association a polypeptide conjugate described herein with liquid carriers (liquid formulation), liquid carriers followed by lyophylization (powder formulation for reconstitution with sterile water or the like), or finely divided solid carriers, or both, and then, if necessary, shaping or packaging the product.

Pharmaceutical compositions of the present disclosure suitable for parenteral administration comprise one or more compounds described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents. In the examples, the active ingredients are brought together with the pharmaceutically acceptable carriers in solution and then lyophilized to yield a dry powder. The dry powder is packaged in unit dosage form and then reconstituted for parental administration by adding a sterile solution, such as water or normal saline, to the powder.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

A library of cyclometalated Ir(III)/Rh(III) metal complexes 1-14 (as racemates) with diverse structures were selected for initial screening, in order to identify favorable substructures for the design of the next round of complexes (FIG. 1a). In cells, HIF-1α moves into the nucleus and binds to the hypoxia-response element (HRE) in the promoters of transactivated genes. In this study, the dual luciferase reporter assay (DLR) was performed to monitor the variations of HRE-driven luciferase activity induced by the complexes (FIG. 1f). Human embryonic kidney HEK293 cells were treated with complexes (10 μM) for 8 h, and the HRE-driven luciferase activity of the cell lysates was determined. Complexes that inhibit the interaction between VHL and HIF-1α would be expected to increase the level of HRE-driven luciferase activity in the cell lysates. The Rh(III) complex Rh(brpy)$_2$(dmeophen) 1 (where brpy=2-(4-bromophenyl)pyridine and dmeophen=4,7-dimethoxy-1,10-phenanthroline) emerged as the top candidate in the first round of screening (FIG. 1b), with slightly higher activity compared to the positive control compound, P1 ((2S)-4-hydroxy-1-(2-(((Z)-2-(3-methoxybenzylidene)-3-oxo-2,3-dihydrobenzofuran-6-yl)oxy)acetyl)pyrrolidine-2-carboxylic acid), a previously reported inhibitor of the VHL-HIF-1α PPI.

Based on the structure of complex 1, a focused library of 14 cyclometalated Rh(III) and Ir(III) complexes containing different CAN or NAN donor ligands were designed and synthesized (1a-1n) (FIG. 1c). This library was enriched in the brpy CAN and dmeophen N^N ligands that were identified in the first round of screening to be favorable substructures for potency. In the second round of screening, the Ir(III) complex 1a, containing two 2-phenylpyridine (ppy) C^N ligands and the dmeophen N^N ligand, showed the highest activation of HRE-drive luciferase activity, and was about twice as potent as both the parent complex 1 as well as the positive control compound P1 (FIG. 1d). Notably, complex 1a demonstrated remarkable stability in a [d$_6$]DMSO/D$_2$O (9:1) solution for at least seven days at 298 K as verified by $^1$H NMR spectroscopy and in acetonitrile/H$_2$O (9:1) solution for at least seven days at 298 K as determined by UV/Vis spectroscopy.

To further investigate the potency of complex 1a at modulating HIF-1α transcriptional activity, a dose-response assay was carried out. The results showed that complex 1a exhibited dose-dependent activation of HRE-driven luciferase activity in HEK293 cells (FIG. 1e). Moreover, the effects of the isolated ligands of complex 1a on HRE-drive luciferase activity were also studied. The results showed that neither brpy nor dmeophen had any significant effect on HRE-drive luciferase activity. This demonstrates the role of Ir(III) center in coordinating the structure of the entire complex in order to confer HIF-1α transcriptional activity.

Figure 2:
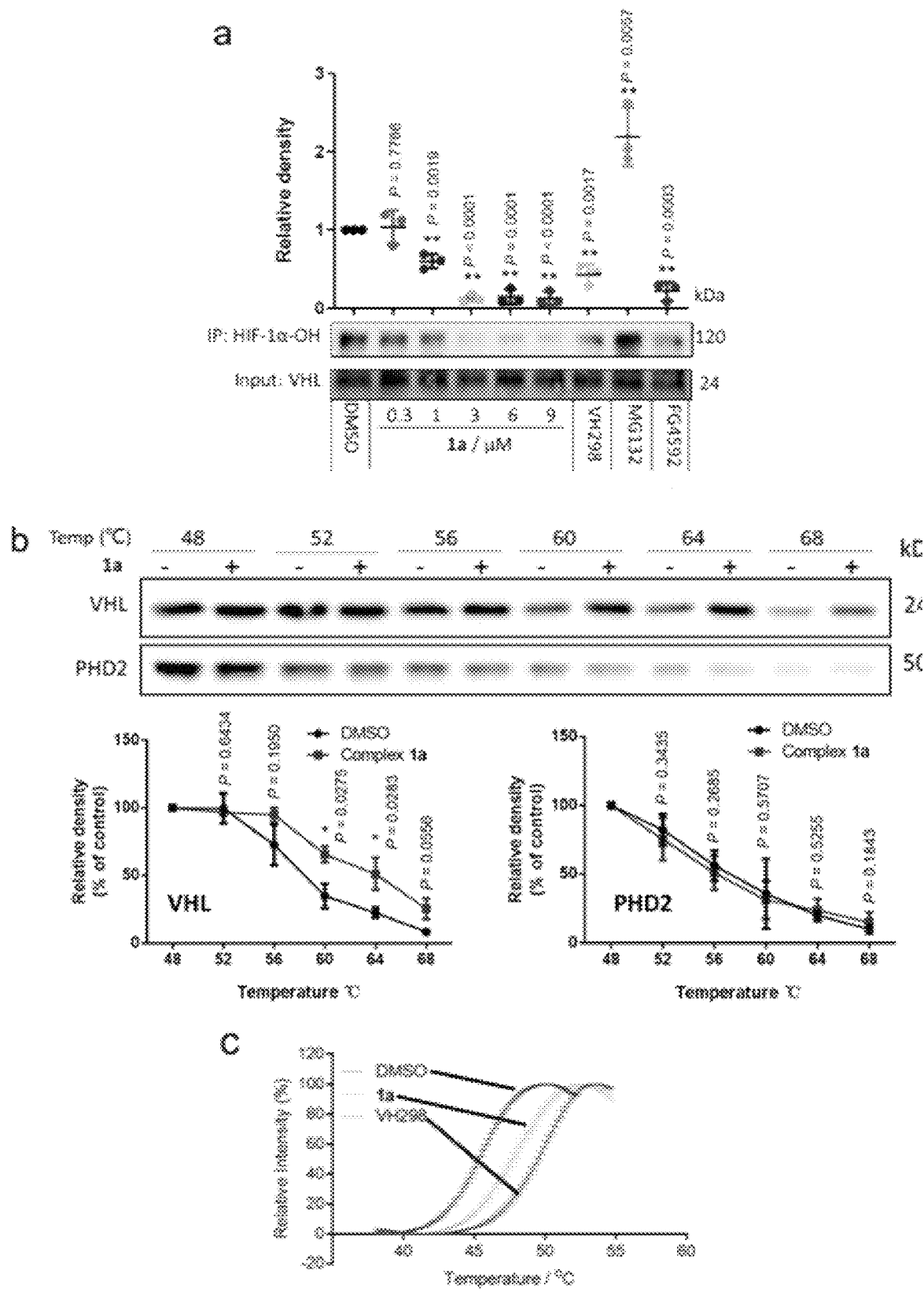
FIG. 2 depicts data demonstrating that complex 1a disrupts the VHL-HIF-1α interaction by selectively engaging VHL. (A) Complex 1a inhibits the interaction of VHL-HIF-1α in cellulo. HEK293 cells were treated with vehicle DMSO (1% for 2 h), 1a (0.3, 1, 3, 6 and 9 μM for 2 h), VH298 (100 μM for 2 h), MG132 (20 μM for 3 h), or FG-4592 (100 μM for 2 h) before lysis. Cell lysates were collected and incubated with VHL antibody overnight at 4° C. The proteins were immunoprecipitated using agarose beads. The levels of hydroxy-HIF-1α co-precipitated with VHL were detected using a hydroxy-HIF-1α antibody, and then visualized using ECL Western Blotting Detection Reagent (GE Healthcare). (B) Cellular thermal shift assays to monitor cellular target engagement of VHL and HIF-1α. HEK293 cell lysates were treated with 1a (3 μM) at room temperature for 30 min and then heated at different temperature ranging from 48° C. to 68° C. for 5 min. The protein samples were collected and detected by Western blotting using either VHL or PHD2 antibodies. (C) Fluorescence-based protein thermal shift assay of VBC in the presence or absence of VH298 (100 μM) and complex 1a (100 μM). (D) ITC titration of complex 1a (300 μM) into recombinant VHL protein (30 μM). ITC experiments were carried in a MicroCal PEAQ-ITC Isothermal Titration Calorimeter (Malvern Panalytical). (E) A competitive fluorescence polarization binding assay was performed to evaluate displacement of a fluorescent peptide (FAM-DEALAHyp-YIPD) binding to VBC ($K_d$=421.50±65.23 nM) by complex 1a. The $IC_{50}$ of complex 1a ($K_d$=2.06 μM) was determined to be 3.79 μM in the presence of 125 nM of the fluorescent peptide and 450 nM VBC using a four-parameter logistic equation. (F) Biolayer interferometry (BLI) kinetic analysis of the interaction between complex 1a and VBC. VBC was surface-immobilized to Ni-NTA biosensors. BLI sensorgrams showing the binding of complex 1a to surface-immobilized VBC. The $K_d$ values for a 1:1 interaction were calculated from the kinetic fit ($K_d$=6.74±0.19 μM) and steady state fit ($K_d$=5.80±0.64 μM), respectively. The Ni-NTA biosensor tips coated with His-tagged VBC were dipped in increasing concentrations of 1a (0.78, 1.56, 3.13, 6.25, and 12.5 μM) to measure binding affinity of 1a to VBC ($k_{on}$=5.22×10² M⁻¹s⁻¹) and subsequently moved to wells containing buffer to measure dissociation rates ($k_{off}$=3.52×10⁻² s⁻¹). Data are expressed as means±SD (n=3 independent experiments for figures a and b, samples for figures c and e), P values were calculated using a two-sided t-test. *P<0.05, **P<0.01 vs. DMSO group.
Figure 2:
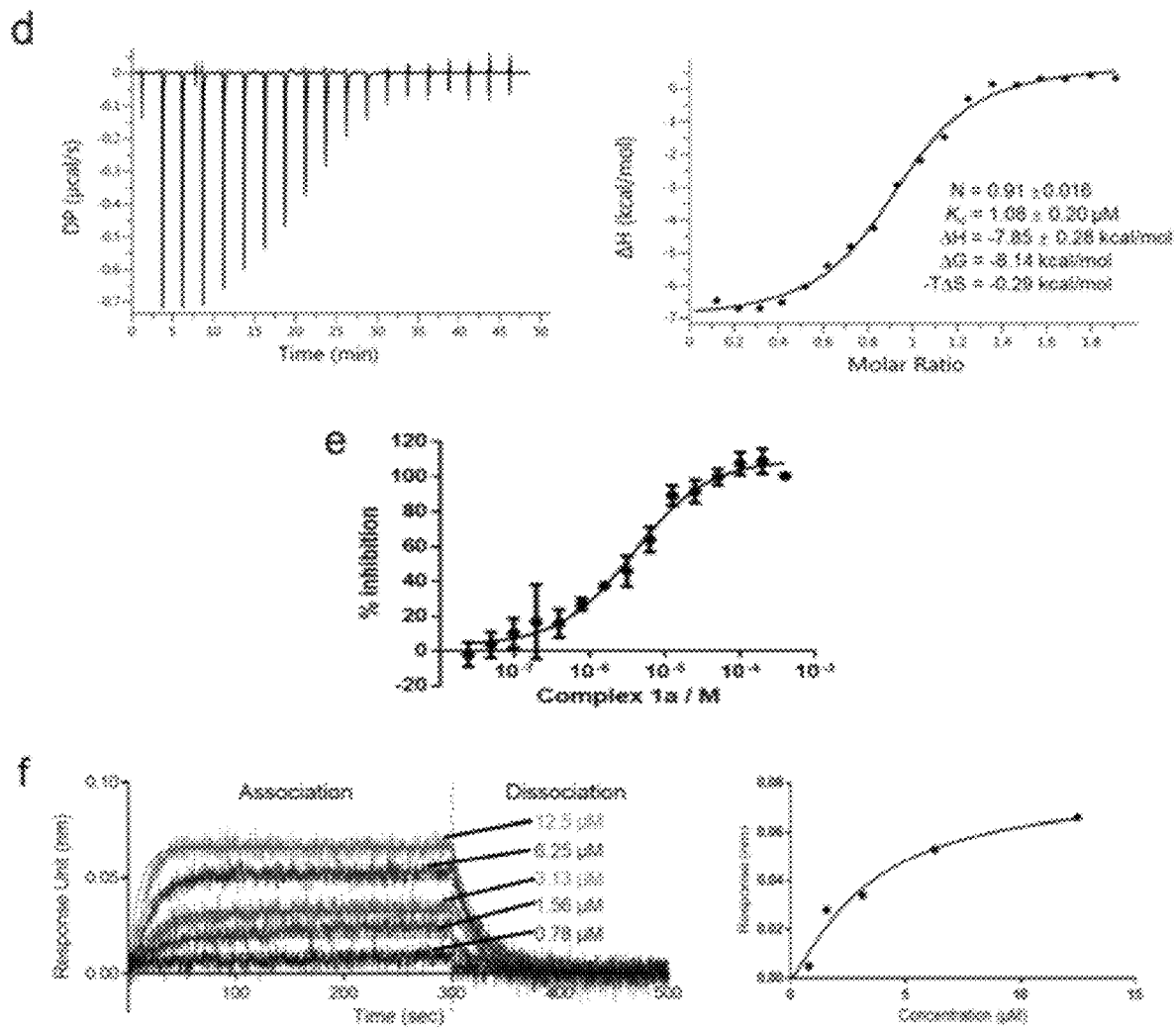

Co-IP experiments were performed to further understand the mechanism of action of complex 1a. HEK293 cells were incubated with complex 1a for 2 h, and cell lysates were subjected to co-IP using VHL antibodies. The results showed that complex 1a reduced the amount of HIF-1α-OH co-precipitating with VHL in a dose-dependent manner, suggesting that it was able to inhibit the VHL-HIF-1α interaction in the treated cells (FIG. 2a).

It is generally known that the efficacy of therapeutics is dependent on the extent of binding of the drug to the target protein. Therefore, the cellular thermal shift assay (CETSA) was performed to verify the engagement between complex 1a and VHL and PHD2. After incubating HEK293 cell lysates with complex 1a followed by heating to set temperatures, VHL and PHD2 levels in the soluble fraction were quantitated by Western blotting. In the presence of complex 1a (3 μM), an obvious shift of about 6° C. in the VHL melting curve was observed (FIG. 2b). This result indicates that complex 1a could stabilize VHL inside cell lysates. In contrast, complex 1a had no appreciable effect on the thermal stabilization of PHD2 (FIG. 2b). We performed further biophysical experiments to demonstrate the direct binding of complex 1a to VHL in vitro. We first prepared plasmids to express and purify human recombinant VHL: ElonginB:ElonginC (VBC) complex, which was verified using a pull-down assay. Circular dichroism (CD) measurements showed a distinct shift of the signal when VBC complex was incubated with 3 μM of 1a in 1% DMSO, while no significant changes were observed with 1% DMSO alone, indicating that 1a could regulate VBC secondary structure via directly binding to VBC complex. VBC's high-affinity interaction with the HIF-1α peptide DEALAHyp-YIPD was also verified, which is involved with mediating the VHL-HIF-1α interface. The stabilization of complex 1a towards VBC was also corroborated using a fluorescence-based protein thermal shift assay (FTS), which revealed by a marked shift of the melting curve (ca. 3.0° C.) of purified VBC in the presence of complex 1a with VH298 (ca. 5.0° C.) as a positive control (FIG. 2c). Meanwhile, isothermal titration calorimetry (ITC) revealed a $K_d$ value of 1.08±0.20 µM (FIG. 2d) between complex 1a and VBC complex, similar to the $K_d$ value of 2.06 µM determined using a competitive fluorescence polarization assay (FIG. 2e). The ITC data in FIG. 2d also indicates that 1a bound to VBC complex with a 1:1 stoichiometry, and that the binding between 1a and VBC is strongly enthalpy-driven ($\Delta G$=−8.14 kcal/mol, −T$\Delta S$=−0.29 kcal/mol, $\Delta H$=−7.85 kcal/mol), suggesting that hydrogen bonds and electrostatic interactions may play a key role in this binding. Moreover, the binding kinetics of 1a from VBC was characterized by BLI (FIG. 2f), which revealed that 1a bound to the immobilized recombinant His-tagged VBC protein complex with $K_d$ values of 6.74±0.19 µM (kinetic fit) and 5.80±0.64 µM (steady state fit). These biophysical experiments are in good agreement for the $K_d$ and stoichiometry for 1a with VBC. Taken together, these data demonstrate that 1a is able to bind to the VBC complex and displace a high-affinity HIF-1α peptide from VBC.

Finally, it was shown that complex 1a was unlikely to activate HIF signaling via oxygen depletion, PHD inhibition, and/or proteasomal inhibition. Similarly, complex 1a had no effect on the level and activity of HIF-2a, which is essential in activating the COX-2 signaling axis in cancer cells. These results suggest that complex 1a selectively targets VHL and inhibits the VHL-HIF-1α interaction.

Figure 3:
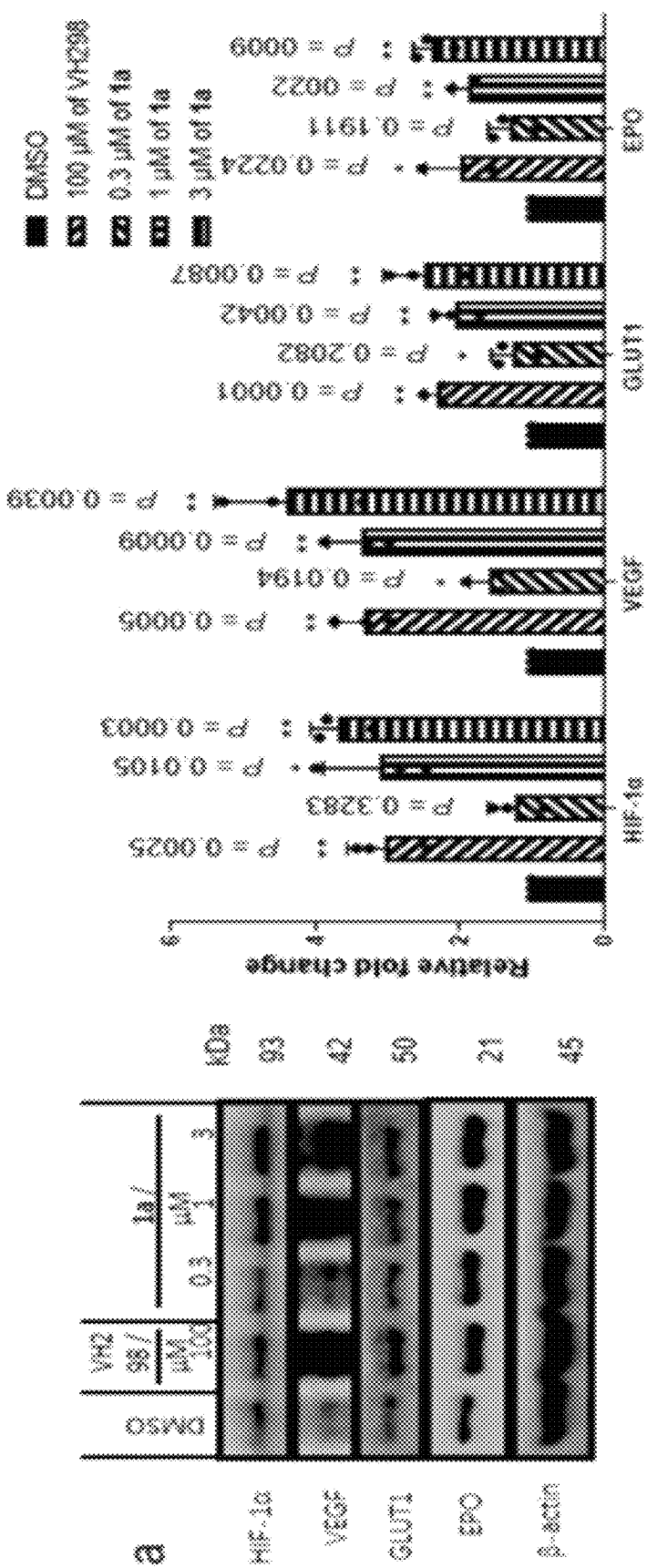
FIG. 3 depicts the effect of complex 1a on HIF-1α target gene products in cellulo. (A) Effect of complex 1a on specific proteins (GLUT1, VEGF, and EPO) mediated by HIF-1α in HEK293 cells. HEK293 cells were treated with 1a for 2 h. Cell lysis were collected and analyzed by the Western blotting. (B) Complex 1a has no effect on HIF-1α accumulation in a VHL null cancer cell line. A498 (VHL-null), or HEK293 cells were treated with 1% DMSO, 1a (3 μM), VH298 (100 μM), and FG-4592 (100 μM) for 2 h before lysis. (C) Effect of complex 1a on EPO, GLUT1, and VEGF levels in HEK293 cells with or without HIF-1α knockdown. Left: The expression levels of EPO, GLUT1, and VEGF in HEK293 cells with or without knockdown HIF-1α in the presence or absence of 1a. Right: Densitometry analysis of EPO, GLUT1, and VEGF levels on the Western blot. HIF-1α siRNA [sense, 5'-CUGAUGACCAGCAACUUGA-3' (SEQ ID NO:1), antisense, 5'-UCAAGUUGCUGGUCAUCAG-3' (SEQ ID NO:2)]. Negative control (NC) siRNA [sense, 5'-UAGCGACUAAACACAUCAA-3' (SEQ ID NO:3), antisense, 5'-UUGAUGUGUUUAGUCGCUA-3' (SEQ ID NO:4)]. Data are expressed as means±SD (n=3 independent experiments), P values were calculated using a two-sided t-test. #P<0.05, P<0.01 HIF-1α siRNA vs. NC siRNA, *P<0.05, **P<0.01 1a vs. vehicle/DMSO group, respectively.
Figure 3:
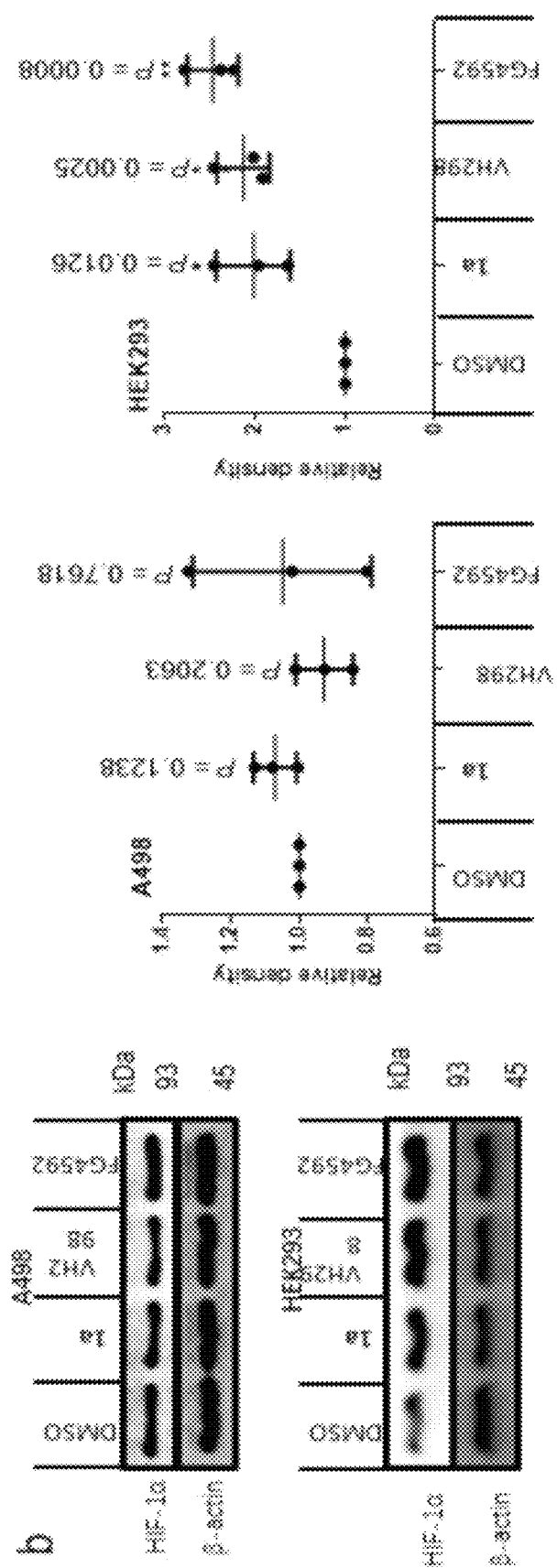
Figure 3:
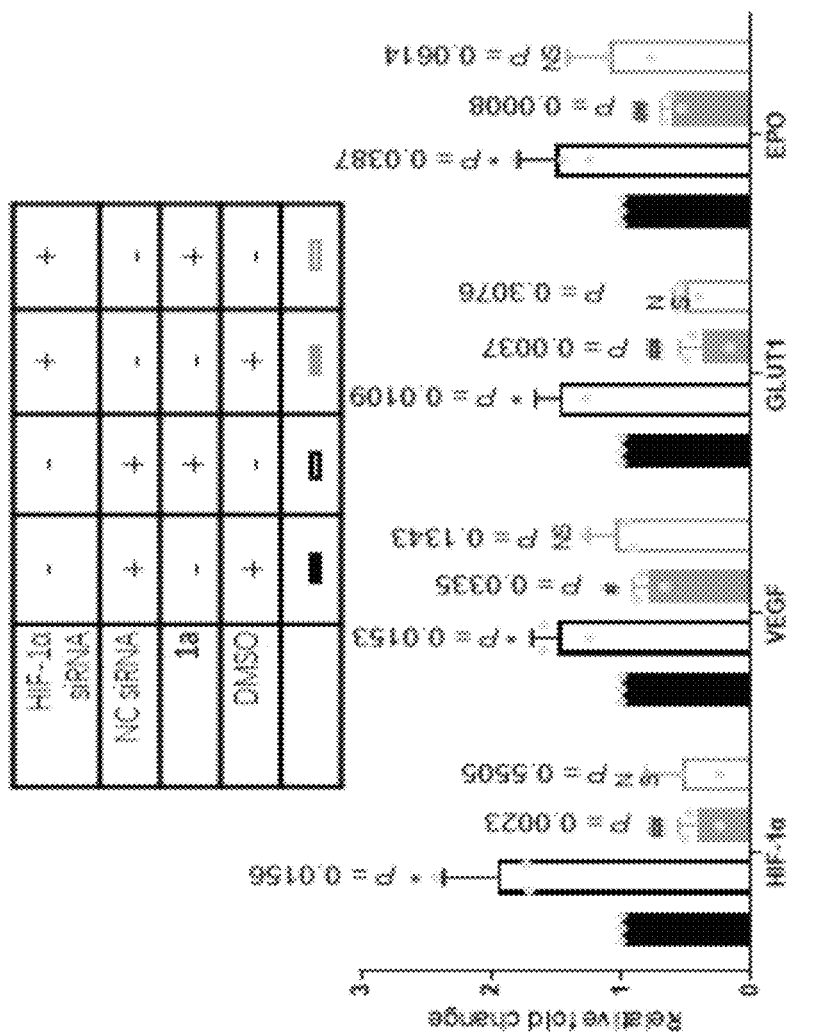
Figure 3:
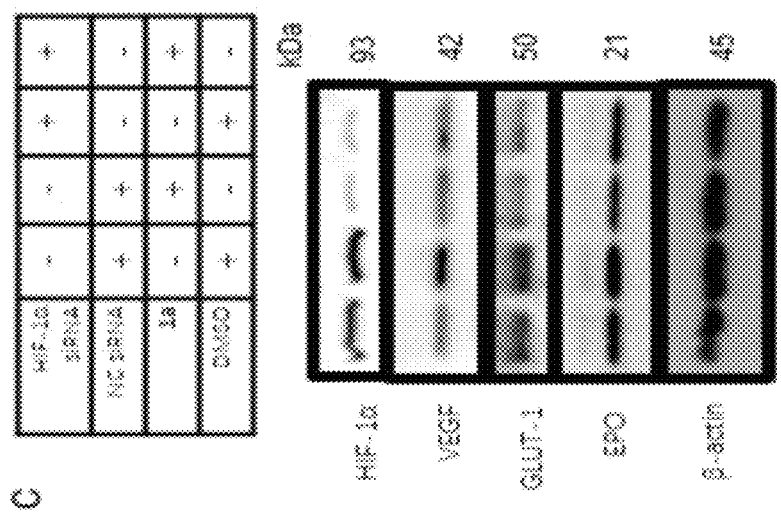

Previous studies have demonstrated that inhibition of the interaction between VHL and HIF-1α results in an accumulation of HIF-1α and the up-regulation of HIF-1α target gene products, including VEGF, GLUT1, and EPO. Therefore, the effect of complex 1a on HIF-1α and HIF-1α target protein levels in cellulo was investigated. After incubation of HEK293 cells with complex 1a for 2 h, the expression levels of HIF-1α, VEGF, GLUT1 and EPO were increased in a dose-dependent manner (FIG. 3a). This can be attributed at least in part to the disruption of the VHL-HIF-1α interaction by complex 1a.

To confirm that the increase of HIF-1α was due to the inhibition of VHL activity, clear cell renal cell carcinoma A498 cells, which lack functional VHL, were treated with 1a or VH298, a potent inhibitor of the VHL-HIF-1α PPI. The PHD inhibitor FG-4592 was also used as a reference compound. As expected, no increase in HIF-1α levels were observed in A498 cells treated with 1a or VH298, whereas HEK293 cells showed a clear accumulation of HIF-1α in the presence of VHL inhibitors (FIG. 3b). These data provide evidence for the stabilization of HIF-1α by 1a via binding to VHL and antagonizing the interaction of VHL-HIF-1α in cellulo.

A knockdown assay was performed to further verify the on-target effect of complex 1a. EPO, GLUT1, and VEGF are target genes regulated by HIF-1α. As expected, knockdown of HIF-1α in HEK293 cells using si HIF-1α reduced the accumulation of EPO, GLUT1, and VEGF compared with control cells (FIG. 3c). Importantly, when compared its effect in normal cells, 1a was less able to increase the accumulation of EPO, GLUT1, and VEGF in HIF-1α knockdown cells. This provides evidence that 1a acts via a HIF-1α-dependent pathway in order to exert its on-target effects in HEK293 cells. However, as only partial effects of HIF-1α knockdown are observed, we do not rule out the possibility that other pathways could be involved in mediating the on-target effects of complex 1a. Taken together, the above results suggest that complex 1a can be developed as a drug candidate for the treatment of human diseases related to impaired angiogenesis or wound healing, resulting from effective and specific blockade of the VHL-HIF-1α interaction.

Figure 4:
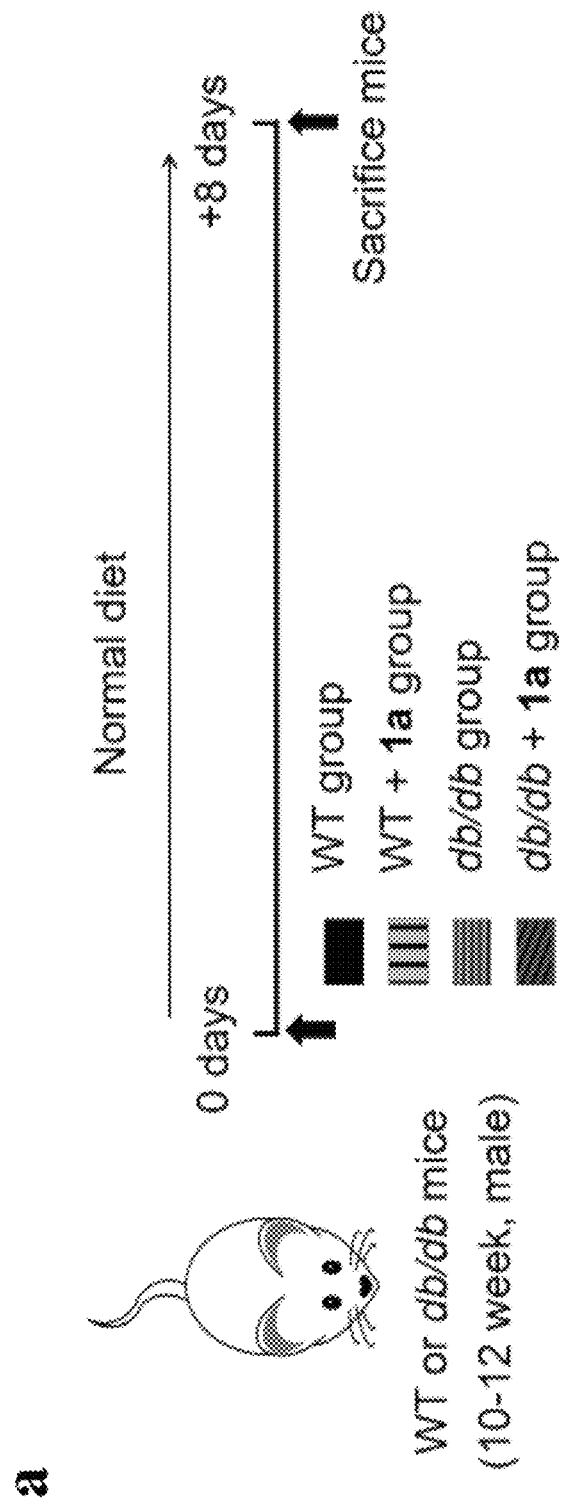
FIG. 4 depicts demonstrating that complex 1a (0.25 mg/mL) accelerates wound closure in db/db mice. (A) Timeline for in vivo experiments. (B) Image of representative wound (left) and wound closure rate (right) (n=5 mice). (C) H&E and Masson's trichrome staining of dorsal skin section and skin thickness from the top of the epidermis to the bottom of the dermis in mice after 8 days post-injury (n=4 mice). Scale bar=200 μm. (D) Laser doppler imager in dorsal skin: representative images were shown for each group (left) and baseline perfusion on back skin of mice (right) after 2 days post-injury (dotted line circle represents the wound bed in mice of each group and arrow represents perfusion intensity (n=5 mice). (E) CD31 and DAPI double staining in wound bed of mice after 8 days post-injury (n=4 mice). Scale bar=50 μm. Data are expressed as means±SD, P values were calculated using a one-way ANOVA with Tukey's multiple comparison test. #P<0.05, ##P<0.01 WT vs. db/db, *P<0.05, **P<0.01 1a vs. vehicle.
Figure 4:
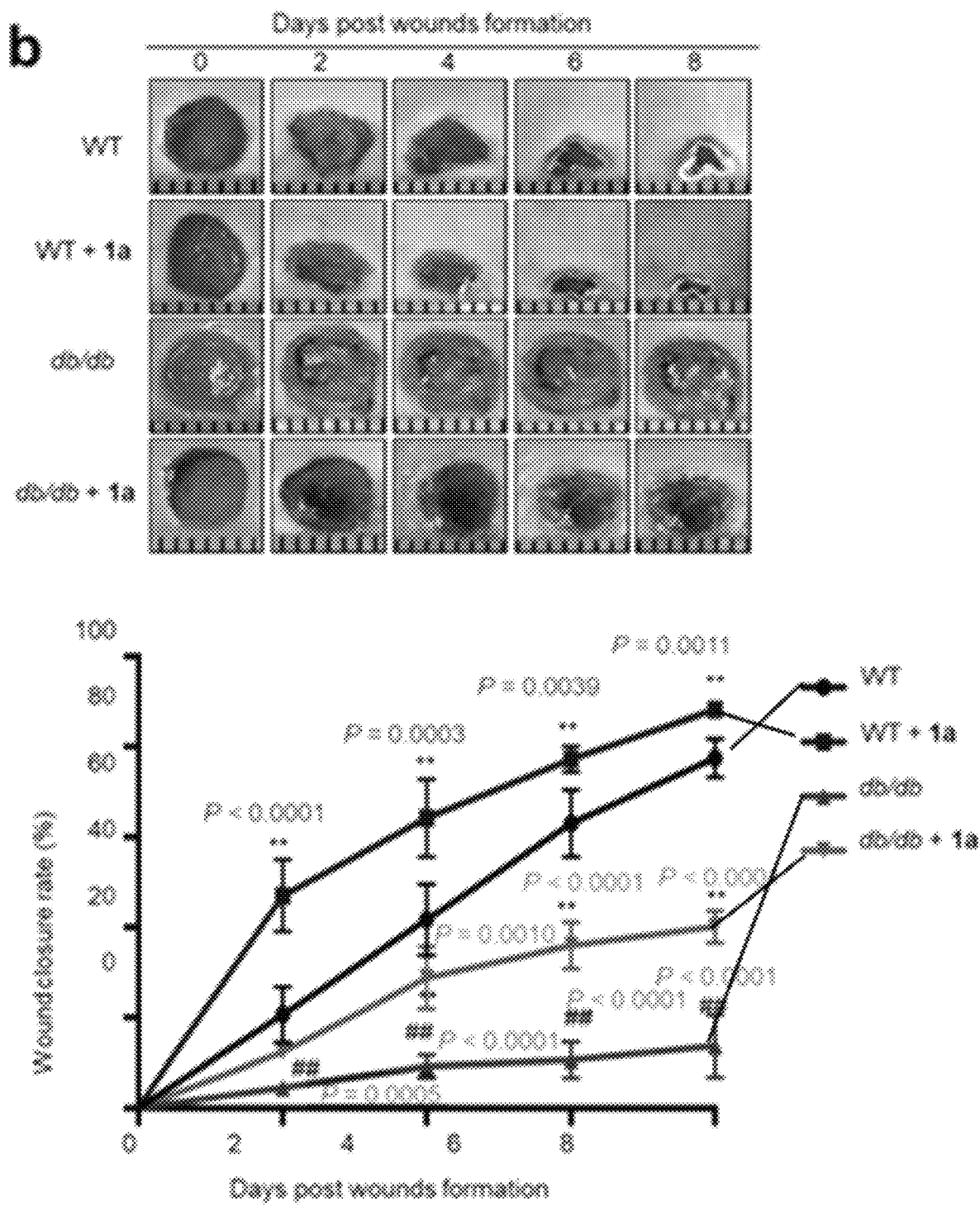
Figure 4:
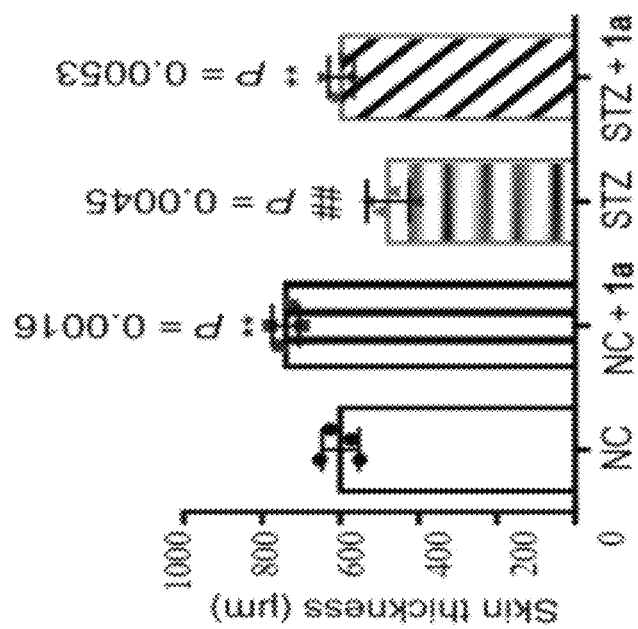
Figure 4:
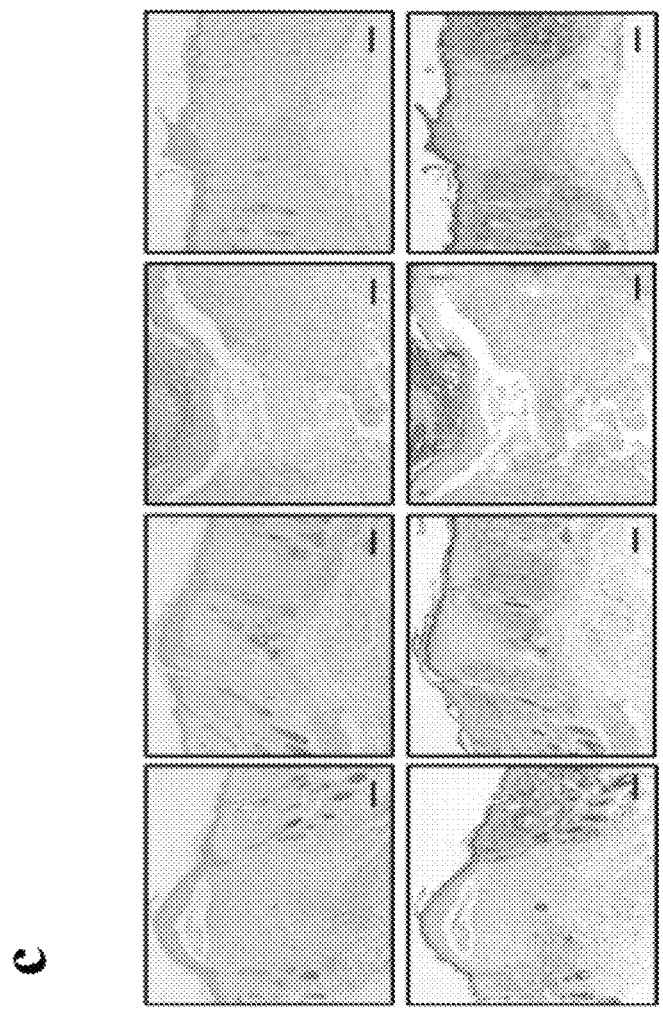
Figure 4:
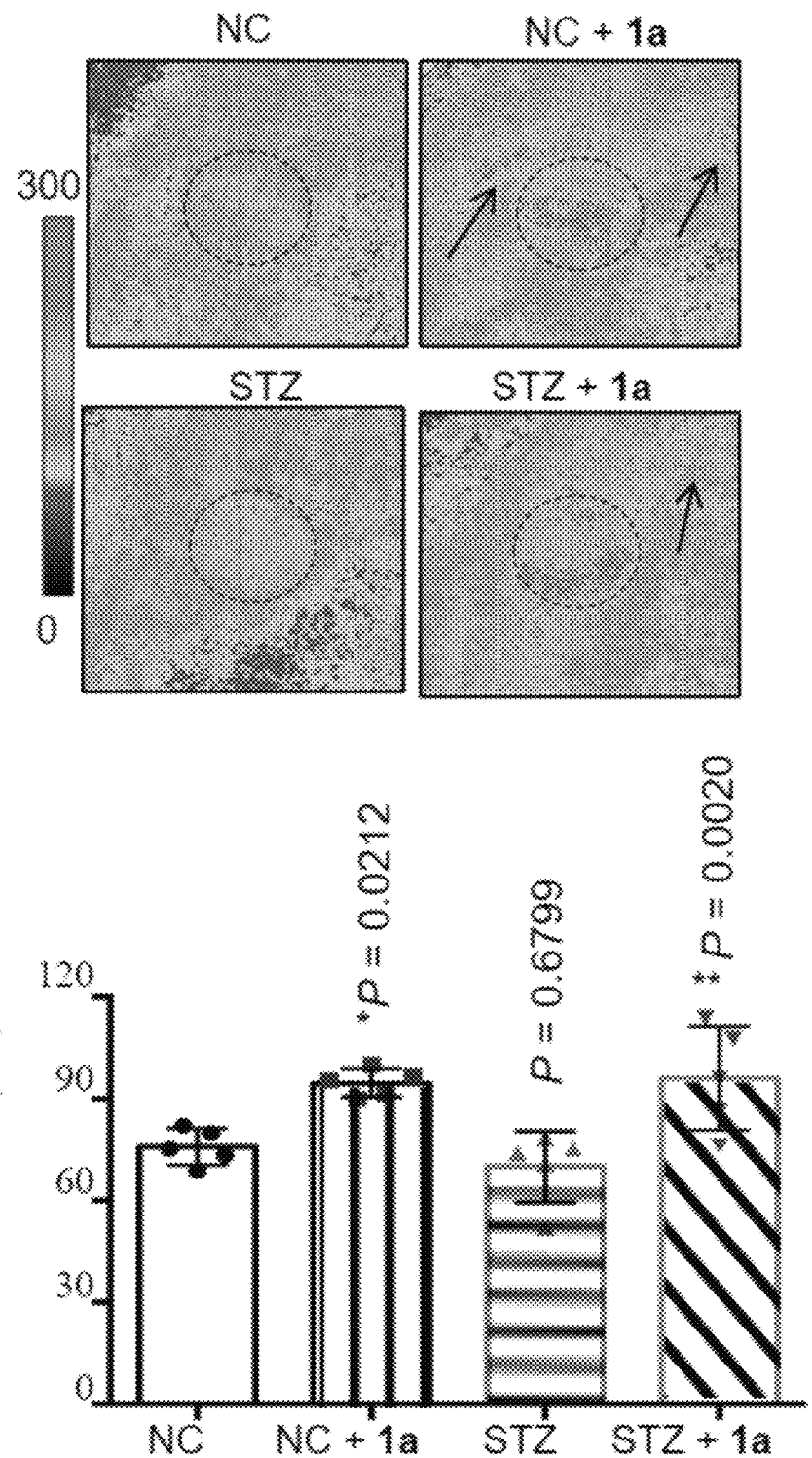
Figure 4:
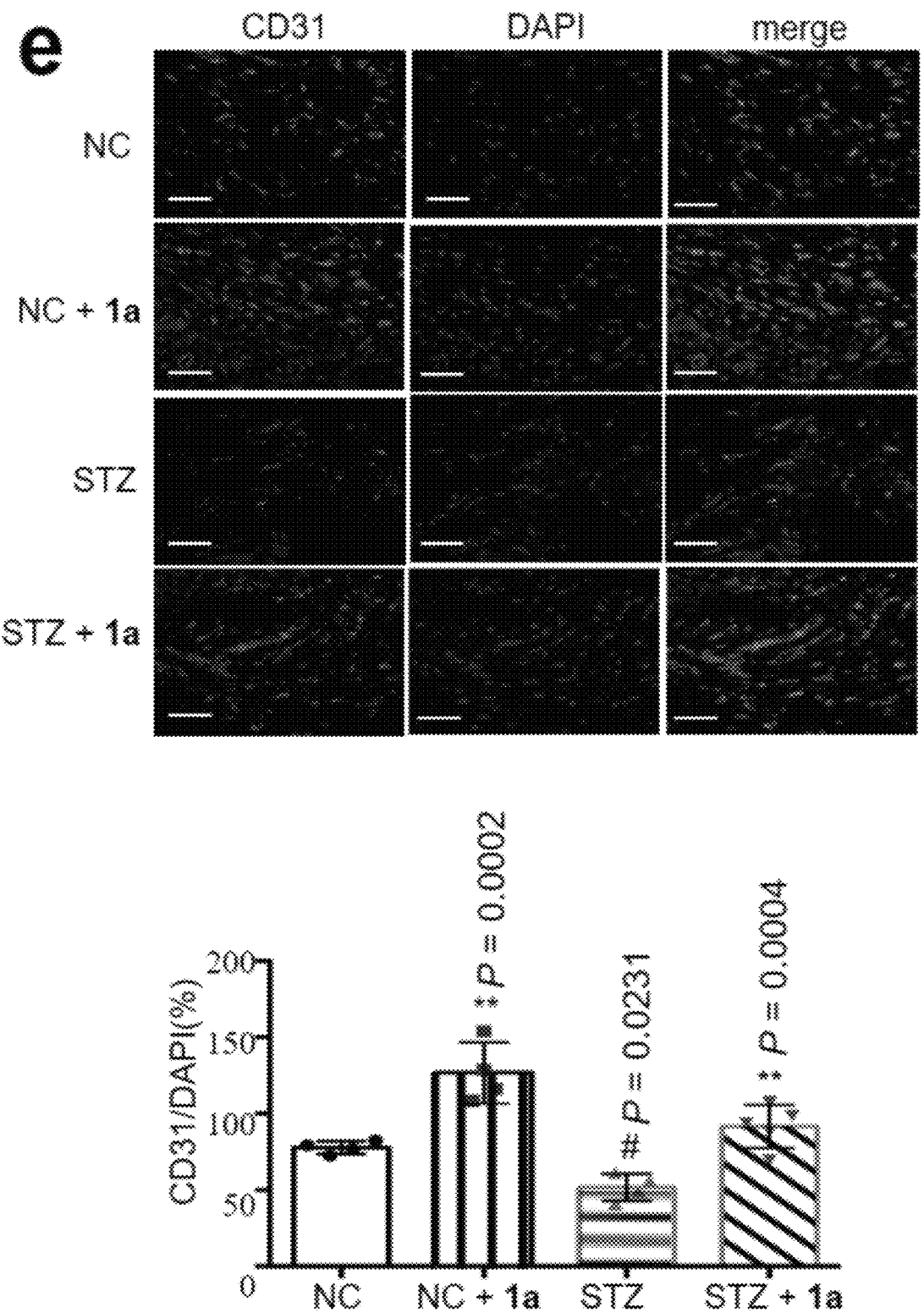

Inspired by the in vitro results, the effect of complex 1a on wound healing in vivo was investigated in leptin-receptor deficient (db/db) diabetic mice, streptozotocin-induced diabetic mice (STZ), and high-fat diet-fed, streptozotocin-treated diabetic mice (HFD/STZ). The db/db and age-matched wide-type (WT) mice were locally administered with vehicle (0.8% w/v Carbopol 974P NF in distilled water, pH 7.0) and 0.25 mg/mL complex 1a (mixed in 0.8% w/v Carbopol 974P NF in distilled water) every other day for 8 days, respectively (FIG. 4a). The local application of complex 1a did not affect body weight during the experimental period, for both WT and db/db mice (Supplementary FIG. 9). STZ mice were obtained by a single injection of high-dose streptozotocin (150 mg/kg) (Supplementary FIG. 10a). HFD/STZ mice were generated by 8 weeks high-fat diet feeding, followed by low-dose streptozotocin injection for 7 days (40 mg/kg/day) (Supplementary FIG. 11a). 3 days after streptozotocin injection, STZ or HFD/STZ mice with fasting blood glucose levels between 15 and 28 mmol/L were considered as diabetic mice and used in wound healing experiments. STZ and HFD/STZ mice were intraperitoneally injected with either vehicle (PEG 400: distilled water=6: 4, v/v) or 1.25 mg/kg complex 1a every other day for 8 days, respectively. Inductively-coupled plasma mass spectrometry (ICP-MS) analysis confirmed the presence of iridium in skin samples of dosed mice from STZ and HFD/STZ mice, demonstrating that complex 1a could reach the target area (Supplementary FIG. 12). In both HFD/STZ and STZ models, neither diabetic nor normal control mice (NC) showed obvious changes in blood glucose levels or body weight after exposure to complex 1a.

In the wound healing experiment, two full-thickness skin lesions were excised in interscapular area of each mouse, and the wound area was monitored every other day. In the WT/NC groups, the rates of wound closure were approximately 21%/22%, 42%/41%, 63%/57%, and 77%/74% after 2 days, 4 days, 6 days, and 8 days post-injury, respectively (FIG. 4b). Treatment of complex 1a in WT/NC mice accelerated wound closure compared to the vehicle group, approaching about 64%/65% of closure after 4 days and almost complete wound closure by 8 days (FIG. 4b). The wound closure rates of the diabetic mice group were lower than those of the WT/NC group on corresponding days; only about 14%, 62% and 44% of the wound was healed after 8 days post-injury for db/db, HFD/STZ and STZ mice, respectively, compared to 77%/74% for WT/NC mice (FIG. 4b). As expected, complex 1a accelerated wound closure in all three diabetic mouse models. The rates of wound closure in 1a-treated db/db mice were about 28% after 4 days and 40% after 8 days post-injury (cf 9% and 14% in untreated db/db mice, respectively) (FIG. 4b); the rates of wound closure in 1a-treated HFD/STZ mice were 62% after 4 days and 82% after 8 days post-injury (cf 30% and 62% in untreated HFD/STZ mice, respectively); and the rates of wound closure in 1a treated STZ mice were 50% after 4 days and 76% after 8 days post-injury (cf 24% and 44% in untreated STZ mice, respectively). Taken together, these results indicate that complex 1a could accelerate wound healing in both normal and diabetic mice, with a greater effect being observed in the diabetic group.

The epithelial thickness of the regenerated skin in each group was compared using H&E staining and Masson's trichrome staining. Encouragingly, in both normal and diabetic mice groups, complex 1a increased skin thickness after 8 days post-injury and also enhanced collagen deposition in wound areas (FIG. 4c). One of the key processes related to wound healing is tissue angiogenesis. Skin perfusion pressure tests indicated that complex 1a remarkably increased skin blood flow rate after 2 days post-injury in both normal and diabetic mice (FIG. 4d, Supplementary FIGS. 10d and 11d). Moreover, CD31 immunostaining images showed that complex 1a significantly enhanced microvessel density in the wound areas in both normal and diabetic groups (FIG. 4e). Taken together, these results indicate that complex 1a is effective at both increasing wound healing and angiogenesis in vivo, in both normal and diabetic mice.

Figure 5:
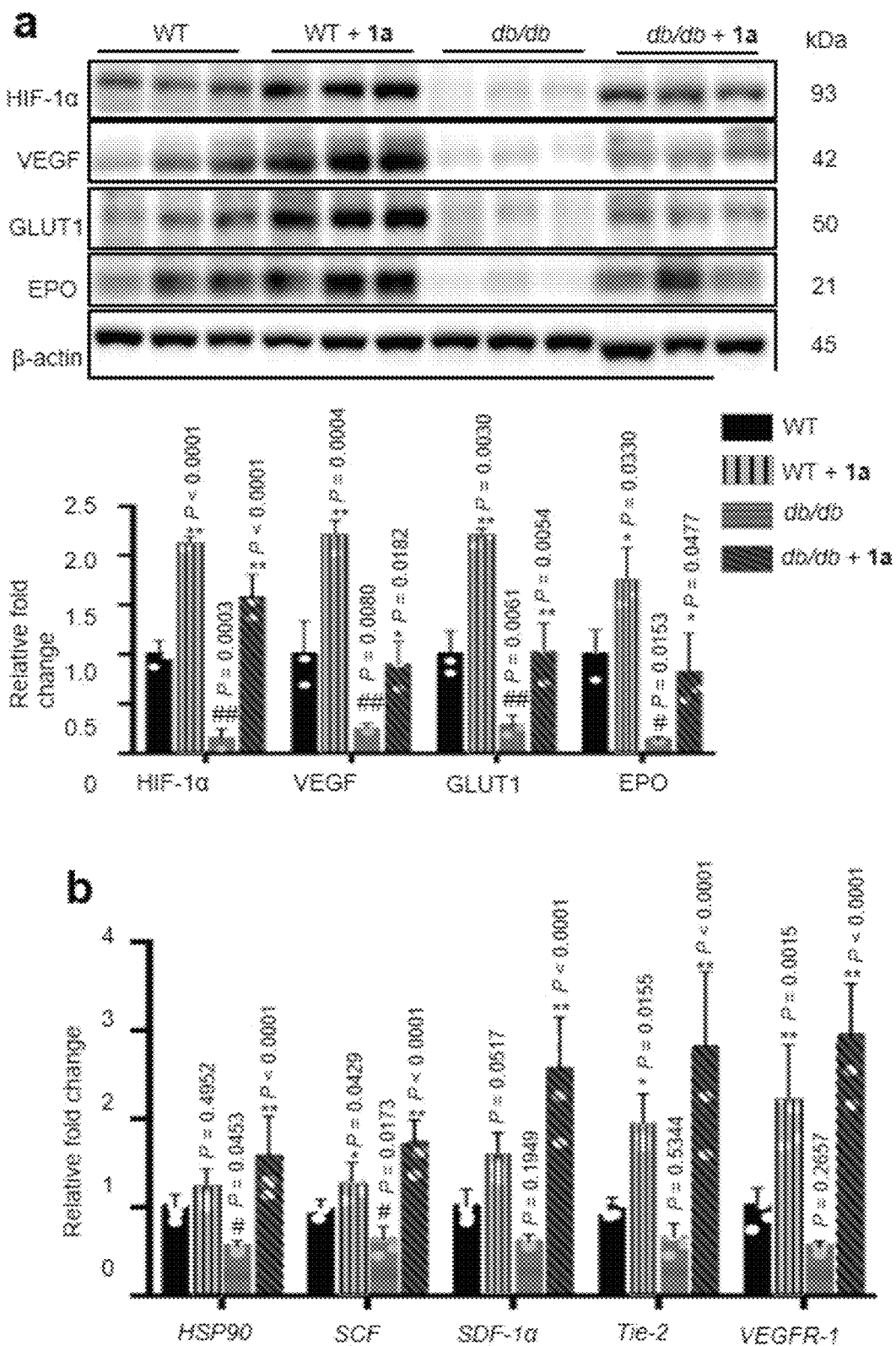
FIG. 5 depicts data demonstrating that complex 1a (0.25 mg/mL) activates gene expression regulated by HIF-1α in db/db mice at 8 days post-injury. (A) Western blot analyses and quantitation of HIF-1α, VEGF, GLUT1, and EPO in wound tissue (n=3 mice). All proteins were normalized by β-actin. (B) The mRNA levels of HIF-1α target genes involved in wound healing were analyzed by qRT-PCR in wound tissues (n=5 mice). Data are expressed as means±SD, P values were calculated using a one-way ANOVA with Tukey's multiple comparison test. P<0.05, P<0.01 WT vs. db/db, *P<0.05, **P<0.01 1a vs. vehicle. S

The expression of HIF-1α, VEGF, GLUT1, and EPO was significantly increased in the wound tissue of 1a-treated WT/NC, db/db, HFD/STZ and STZ groups at 8 days post-wounding, compared with the vehicle mice as shown by Western blotting (FIG. 5a). The expression levels of HIF-1α and its target genes were significantly lower in the diabetic group compared to the WT/NC group, demonstrating that HIF-1α signal transduction was impaired (FIG. 5a). Moreover, HIF-1α target genes essential for wound healing cell motility (i.e. HSP-90), angiogenesis (i.e. VEGFR-1), and recruitment of CAG (i.e. SDF-1, SCF, and Tie-2) were also increased in the wound tissue of 1a-treated diabetic mice as revealed by qRT-PCR, with weaker effects being observed in the WT/NC mice (FIG. 5b). Taken together, these results therefore provide a mechanistic basis for the observed enhancement of wound healing and angiogenesis induced by complex 1a in diabetic mice.

In this study, the Ir(III) complex 1a was ascertained to be the first metal-based inhibitor of the VHL-HIF-1α interaction. Complex 1a was identified after two rounds of screening, allowing preliminary structure-activity relationship (SAR) trends to be drawn for this series of compounds. In the first round of screening, the Rh(III) complex 1, containing two brpy C^N ligands and a 4,7-dmeophen N^N ligand, displayed the highest activation of HIF-1α transcriptional activity (FIGS. 1a and 1b). As no other complexes in the first round of screening contain bromine groups, this could suggest the importance of the bromine group in activating HIF-1α activity. Complex 9, containing fluorine groups, showed low activity, indicating that fluorine is less preferred than bromine for potency. Moreover, complexes 6 and 7 bearing C^N ligands derived from 2-phenylquinoline (phq) also showed low activity, suggesting that C^N ligands based on 2-phenylpyridine (ppy) are more favored. After complex 1, the Rh(III) complex 5 containing the 4,7-diphenyl-1,10-phenanthroline (dpphen) N^N ligand was the next most potent candidate. This suggests that conjugating phenyl groups to the 1,10-phenanthroline (phen) N^N ligand could also be somewhat tolerated, although the methoxy groups of 4,7-dmophen (as in complex 1) were still preferred for activating HIF-1α transcriptional activity.

A focused library of 14 cyclometalated Rh(III) and Ir(III) complexes (1a-1n) containing different C^N or N^N donor ligands were subsequently synthesized based on the structure of the lead complex 1 (FIG. 1c). Analysis of the data from the second round of screening (FIG. 1d) revealed additional SAR trends. The most potent complex 1a, bearing containing two 2-phenylpyridine (ppy) C^N ligands and the dmeophen N^N ligand, is substantially more active than the Rh(III) congener 1b, indicating that the Ir(III) metal center is very important for the biological potency of 1a. In contrast, the Ir(III) congener (1c) of the original parent Rh(III) complex 1 showed drastically reduced activity, indicating that for this combination of C^N and N^N ligands, the Rh(III) center is greatly preferred. Upon comparing the Ir(III) complexes 1c and 1a, it can be seen that changing the C^N ligand from brpy (as in 1c) to ppy (as in 1a) vastly improves the activity of the complex. After 1a, the second-most potent compound was the Ir(III) complex 1g, which differs from 1a only by the presence of an additional methyl group at the 8-position of the ppy C^N ligand. However, adding a methyl group to the 6-position of the ppy ligand (as in 1e) substantially weakens the activity of the complex, indicating that steric factors are highly important for the interaction of the complexes with the target. Upon comparing the N^N ligands, it can be seen that the dmeophen ligand of the parent complex still remains the preferred scaffold. For example, changing from 1a to 1h, which has the 4,4'-dimethoxy-2,2'-bipyridine (dmobpy) ligand rather than dmeophen, led to a decrease in activity, indicating that the additional fused phenyl ring in 1a is important for biological potency. Replacing the two methoxy groups of 1a with hydrogen groups (as in 1i or 1j), bromine groups (as in 1k or 1l) or phenyl groups (as in 1m or 1n) also led to drastically reduced activity for both the Rh(III) and Ir(III) congeners, respectively. This indicates that the biological activity of the complexes is highly sensitive to the nature of the substituents on the N^N ligand.

Complex 1a selectively targeted VHL in vitro as revealed by CETSA and biophysical experiments (including ITC, FP, and BLI), leading to the disruption of the VHL-HIF-1α interaction in cellulo as shown by co-IP, and the stimulation of HIF-1α-directed signaling as revealed using the DLR assay. Moreover, complex 1a effectively up-regulated HIF-1α target gene products in cellulo. HIF-1α levels are decreased under hyperglycemia[16]. In murine diabetes models, complex 1a induced the accumulation of HIF-1α and the activation of HIF-1α-driven genes that are important for angiogenesis, including VEGFR, SDF-1α and SCF. Importantly, complex 1a significantly improved wound healing and angiogenesis in diabetic mice. This study therefore demonstrates the validity of inhibiting the VHL-HIF-1α interaction as a therapeutic avenue for diabetic wound healing via both topical and intraperitoneal delivery routes.

VH298 is the most effective VHL-HIF-1α protein-protein interaction inhibitor described to date, and has ca. 100-fold stronger binding affinity to VHL than complex 1a. VH298 engages with high affinity and specificity with VHL as its only major cellular target, leading to selective on-target accumulation of hydroxylated HIF-α in a concentration- and time-dependent fashion in different cell lines. As an alternative scaffold class, the metal complex 1a has shown promising wound healing results in in vivo models of diabetes. In this study, HFD/STZ mice were prepared through a high-fat diet with subsequent multiple injections of a low dose of STZ. The key advantage of this model is to mimic the slow pathogenesis of type 2 diabetes that occurs in humans, encompassing the slow development from adult-onset diet-induced obesity to glucose intolerance, insulin resistance, the resulting compensatory insulin release and finally STZ-induced partial 3-cell death. In this type 2 diabetes model, complex 1a showed promising wound healing activity when administered via intraperitoneal injection. Additionally, the topical application of complex 1a was performed on another widely used diabetic model, db/db mice, to confirm that our compound could also promote wound closure when applied externally.

While the binding affinity of complex 1a is around 100-fold lower than that of the existing VHL-HIF-1α inhibitor VH298, it is demonstrated that administering complex 1a at higher dosages (over 30-fold higher compared to the dosage of VH298 used in a previous study) and through various routes can lead to a significant accumulation of complex 1a at injured skin tissue and promising wound healing effects in animal models of diabetes (including db/db, HFD/STZ and STZ) without significant toxicity. Hence, this report provides an additional scaffold for the development of wound healing therapeutics, and also validates the feasibility of VHL-HIF-1α inhibitors on treating diabetic wounds through different routes of drug administrations, including intraperitoneal injection and topical application.

EXAMPLES

Example 1—General Synthesis of [M$_2$(C^N)$_4$Cl$_2$] Complexes

Cyclometalated dichloro-bridged dimers of the general formula [M$_2$(C^N)$_4$Cl$_2$], where M=Ir(III)/Rh(III), were synthesized as follows. In brief, MCl$_3$·3H$_2$O was heated to 130° C. with 2.2 equivalents of the C^N ligand in 3:1 methoxymethanol and deionized water under a nitrogen atmosphere for 12 h. The reaction was cooled to room temperature, and the product was filtered and washed with three portions of deionized water and then three portions of ether (3×50 mL) to yield the corresponding dimer.

Example 2—General Synthesis of [M(C^N)$_2$(ACN)$_2$]OTf Complexes

[M$_2$(C^N)$_4$Cl$_2$] was mixed with 2.0 equivalents of silver triflate in 25 mL acetonitrile and stirred at room temperature under a nitrogen atmosphere for 15 h. The mixture was filtered and washed with two portions of ether (2×30 mL) to yield titled product.

Example 3—General Synthesis of [M(C^N)$_2$(N^N)]PF$_6$ Complexes

A suspension of [M$_2$(C^N)$_4$Cl$_2$] (0.2 mM) and corresponding N^N (0.44 mM) ligands in a mixture of dichloromethane:methanol (1:1, 20 mL) was refluxed overnight under a nitrogen atmosphere. The resulting solution was allowed to cool to room temperature, and was filtered to remove the unreacted cyclometalated dimer. To the filtrate, an aqueous solution of ammonium hexafluorophosphate (excess) was added and the filtrate was reduced in volume by rotary evaporation until precipitation of the crude product occurred. The precipitate was then filtered and washed with several portions of water (2×50 mL) followed by diethyl ether (2×50 mL). The product was recrystallized by acetonitrile:diethyl ether vapor diffusion to yield the titled compound. Complexes 1-14 and 1a-1m were characterized by $^1$H-NMR, $^{13}$C-NMR, high resolution mass spectrometry (HRMS) and elemental analysis.

Example 4—Transient Transfection

HEK293 cells were seeded in six well plates 24 h before transfection. HRE-luciferase plasmid (4 μg) and pRL-TK plasmid (4 μg) and TurboFect reagent (6 μL) were mixed together in serum-free DMEM medium and the resulting solution was incubated for 20 min at room temperature. The mixture was the added dropwise to the HEK293 cells in the wells. The cells were incubated for 32 h at 37° C. in a CO$_2$ incubator before use.

Example 5—Dual Luciferase Reporter Assay

The inhibition of HIF-1α activity was assayed by a reporter assay using a dual luciferase reporter assay system (Promega, Madison, WI, USA). Transiently transfected cells were treated with complexes or P1 for 8 h before measurement. Luciferase activity was integrated over a 10 second period and measured using a spectrophotometer (Spectramax M5, Molecular Devices, USA). The results were standardization with the activity of *Renilla* luciferase. All data are expressed as means±SD.

Example 6—Co-Immunoprecipitation

The inhibition of VHL-HIF-1α interactions was investigated using a co-immunoprecipitation assay following the manufacturer's instructions. Briefly, HEK293 cells (1×10$^6$ cells/well) were treated with indicated concentrations of complex 1a, P1 (30 μM) or DMSO for 2 h. After cell lysis and protein lysate separation, 100 μg of total protein was incubated with VHL antibody (1:1000; GTX101087, GeneTex) at 4° C. overnight. The proteins were immunoprecipitated using agarose beads. The levels of co-precipitated HIF-1α-OH were visualized using ECL Western Blotting Detection Reagent (GE Healthcare).

Example 7—Western Blotting

After electrophoresis of protein samples (30 μg of total protein) on SDS-PAGE gels, the samples were transferred to a PVDF membrane and incubated at room temperature with blocking solution for 1 h. The membrane was treated with primary antibodies and incubated overnight at 4° C. After 1 h incubation with the secondary antibodies (Supplementary Table Sl), protein bands were visualized using ECL Western Blotting Detection Reagent (GE Healthcare).

Example 8 Cellular Thermal Shift Assay

Cellular thermal shift assay was performed to monitor the target engagement of 1a in HEK293 cell lysates. Briefly, 1×10$^6$ HEK293 cells were lysed and lysates were collected, diluted in PBS and separated into aliquots. Each aliquot was treated with 1a (10 μM) or DMSO. 30 min after incubation at room temperature, the complex-treated lysates were divided into 50 μL in each of PCR tubes and heated individually at different temperatures (Veriti thermal cycler, Applied Biosystems/Life Technologies). The heated lysates were centrifuged and the supernatants were analyzed SDS-PAGE followed by immunoblotting analysis by probing with antibodies.

Example 9—Isothermal Titration Calorimetry

ITC experiments were carried in a MicroCal PEAQ-ITC Isothermal Titration Calorimeter (Malvern Panalytical)[22]. Briefly, complex 1a and recombinant VBC complex were dialyzed into the ITC buffer (20 mM Bis-Tris, 150 mM NaCl, 2 mM DTT, 1% DMSO) overnight. Complex 1a (300 μM) was titrated against 30 μM VBC complex, consisting of 19 injections of 2 μL complex 1a solution at a rate of 2 sec/μL at 150 s time intervals. An initial injection of ligand (0.4 μL) was made and discarded during data analysis. The experiment was carried out at 25° C. while stirring at 750 rpm. The generated data were fitted to a single binding site model using the Setup MicroCal PEAQ-ITC Analysis Software provided by the manufacturer. Three control titrations, in which (1) 1a is titrated into VBC buffer; (2) VBC buffer is titrated into VBC complex; (3) VBC buffer is titrated into VBC buffer, were also analyzed by using composite model.

Example 10—Biolayer Interferometry

The binding affinities of inhibitors to recombinant VBC were measured by biolayer interferometry on an OctetRed 96 (Fortebio). Ni-NTA biosensors were loaded with 25 μg/mL His-tagged VBC in BLI kinetics buffer (PBS buffer containing 0.02% Tween 20 and 0.1% BSA) with a binding value of ca. 5.5 nm, washed in the same buffer and transferred to wells containing complex 1a or HIF-1α peptide at indicated concentrations in the same buffer. The Ni-NTA biosensor tips coated with His-tagged protein complex were dipped in increasing concentrations of 1a or HIF-1α for 300 s and subsequently dissociated in the wells containing buffer for another 300 s. Negative control performed with BLI kinetics buffer against Ni-NTA biosensors was subtracted from the sample response against VBC-loaded Ni-NTA biosensors. The equilibrium dissociation constant ($K_d$) value for a 1:1 interaction was calculated from the kinetic fit and steady state fit, respectively. The $K_d$ and associated standard errors were calculated using Octet analysis software.

Example 11—Knockdown Assay

HEK293 cells were seeded in 6-well plate at 80% confluence in DMEM medium for 24 h. Lipofectamine 3000 reagent and siRNA was gently mixed and incubated for 15 min at room temperature. Remove growth medium from cells and replace with 0.5 mL of fresh medium. Then the mixture 500 μL were added to each well. Cells were incubated at 37° C. in a $CO_2$ incubator for 72 h post-transfection before the further research.

Example 12—Animal Experimental

Male db/db mice were purchased from the Model Animal Research Center of Nanjing University (Nanjing, China). Male C57BL/6J mice were purchased from the animal facility of Faculty of Health Sciences, University of Macau. All mice were housed in the animal facility of University of Macau, maintained at 23±1° C. (50%±5% relative humidity) with 12 h light/dark cycles with free access to water and regular chow diet. For the db/db model, 10-12 weeks old WT and db/db mice were randomly divided into two groups, respectively. The vehicle and 1a groups were locally treated with vehicle (0.8% w/v Carbopol 974P NF in distilled water, pH 7.0, Chineway, Shanghai, China) or 0.25 mg/mL complex 1a (mixed in 0.8% w/v Carbopol 974P NF in distilled water) every other day for 8 days. For the STZ model, 10-12 weeks old mice were randomly divided into two groups. One group of mice were intraperitoneally injected with streptozocin (150 mg/kg body weight, 0.1 M citrate buffer, pH 4.5, Sigma-Aldrich, St. Louis, MO, USA) to induce diabetes, and the other group of mice were intraperitoneally injected with the same volume of citrate buffer (NC). The mice were maintained for 3 days. After fasted for 6 h, the blood glucose levels were measured by One-Touch Ultra glucometer (Lifescan, Milpitas, CA, USA). For the HFD/STZ model, 6-8 weeks old mice were randomly divided into two groups, fed a regular chow diet (NC) or high-fat diet (HFD, 60% calories from fat, Trophic Animal Feed High-Tech Co., Nantong, Jiangsu, China) for 8 weeks. Then, the HFD-fed mice were received daily intraperitoneal injection of streptozocin (40 mg/kg) for 7 days. For STZ and HFD/STZ models, the mice with blood glucose between 15.0 and 28.0 mmol/L, accompanied with manifestations of polydipsia, polyuria and polyphagia, were considered to be diabetic mice for the following experiments. The NC, STZ and HFD/STZ mice were randomly allocated into two groups, respectively. The vehicle and 1a groups were intraperitoneally injected with vehicle (PEG 400: distilled water=6:4, v/v) and 1.25 mg/kg complex 1a every other day for 8 days. All animal experiments were approved by the Animal Ethical and Welfare Committee of University of Macau (No. ICMS-AEC-2014-06). All experiments complied with all relevant ethical regulations.

Example 13—Skin Wound Model

Mice were anesthetized by inhalation of 3% isoflurane. Prior to excision for wounds, dorsal hair was shaved with an electric clipper followed by a depilatory cream. The skin was rinsed with alcohol and two full-thickness wounds extending through the panniculus carnosus were created on the dorsum on each side of midline, using a 6-mm biopsy punch. Digital photographs were recorded at the day of surgery and every other day post-injury. A circular reference was placed alongside to permit correction for the distance between the camera and the animals. Wound area was quantitated using ImageJ (National Institutes of Health); wound closure rates were calculated as the following formulation: (wound area on day 0−wound area on day X)/wound area on day 0×100%.

Example 14—Histological Analysis and Microvessel Density Assay

After fixation in 4% paraformaldehyde, the skin samples were embedded in paraffin and sectioned (5 m). For histological evaluation, sections were deparaffinized and rehydrated followed by hematoxylin and eosin (H&E) and Masson's trichrome staining. For immunohistochemical staining of CD31, the wound tissue sections were deparaffinized and stained with CD31 antibody (1:1000; ABclonal, Cambridge, MA, USA). The slides were examined under ×400 magnification to identify the area with the highest vascular density, and five randomly high-power field areas of the highest microvessel density were selected for each section. The average was calculated as the microvessel density of this sample.

Example 15—Statistical Analysis

Data were analyzed using GraphPad Prism 6.0 software. All experimental data were presented as mean±SD (standard deviation), and each experiment was performed a minimum of three times. Significant differences between groups were determined using a one-way analysis of variance (ANOVA) unless otherwise noted. $P<0.05$ was considered statistically significant throughout the study.

What is claimed is:

1. A method of promoting wound healing in a subject in need thereof, die method comprising: administering a therapeutically elective amount of a metal complex of Formula 1 and a pharmaceutically acceptable anion, wherein the metal complex of Formula 1 has the structure:

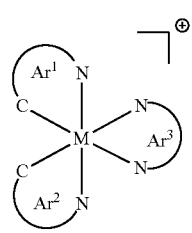

1 wherein M is Ir (III) or Rh (III);

each of $Ar^1$ and $Ar^2$ is independently:

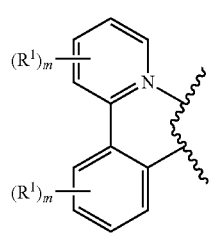

wherein in for each instance is independently a whole number selected from 0-2; and $R^1$ for each instance is independently selected from the group consisting of halide, nitro, nitrile, azido, —$OR^3$, —$OP(O)(OR^3)_2$, —$SR^3$, —$N(R^3)_2$, —$P(O)(OR^3)_2$, —$C(O)R^3$, —$C(O)OR^3$, —$OC(O)R^3$, —$N(R^3)C(O)R^3$, —$C(O)N(R^3)_2$, —$N(R^3)C(O)OR^3$, —$OC(O)N(R^3)_2$, —$OC(O)OR^3$, —$N(R^3)C(O)N(R^3)_2$, —$S(O)_2R^3$, —$S(O)_2OR^3$, —$S(O)_2N(R^3)_2$, —$N(R^3)S(O)_2R^3$, alkyl, haloalkyl, perhaloalkyl, alkenyl, alkynyl, cycloalkyl, heterocycloalkyl, aryl, heteroaryl, aralkyl, and —(CR$^4_2$)$_p$A, wherein p for each instance is independently a whole number selected from 1-10; R$^4$ for each instance is hydrogen, alkyl, cycloalkyl, aryl, or heteroaryl; and A for each instance is independently halide, nitrite, nitro, azido, —OR$^3$, —SR$^3$, —N(R$^3$)$_2$, —C(O)R$^3$, —C(O)OR$^3$, —OC(O)R$^3$, —N(R$^3$)C(O)R$^3$), —C(O)N(R$^3$)$_2$, —N(R$^3$)C(O)OR$^3$, —OC(O)N(R$^3$)$_2$, —OC(O)OR$^3$, —N(R$^3$)C(O)N(R$^3$)$_2$, —S(O)$_2$R$^3$, —S(O)$_2$N(R$^3$)$_2$, —N(R$^3$)S(O)$_2$R$^3$, alkynyl, heterocycloalkyl, aryl, heteroaryl, and aralkyl;

Ar$^3$ is;

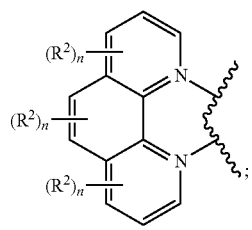

wherein n for each instance is independently a whole number selected from 0-2;

R$^2$ for each instance is independently selected from the group consisting of halide, nitro, nitrile, azido, —OR$^3$, —OP(O)(OR$^3$)$_2$, —SR$^3$, —N(R$^3$)$_2$, —P(O)(OR$^3$)$_2$, —C(O)R$^3$, —C(O)OR$^3$, —OC(O)R$^3$, —N(R$^3$)C(O)R$^3$, —C(O)N(R$^3$)$_2$, —N(R$^3$)C(P)OR$^3$, —OC(O)N(R$^3$)$_2$, —OC(O)OR$^3$, —N(R$^3$)C(O)N(R$^3$)$_2$, —S(P)$_2$R$^3$, —S(O)$_2$OR$^3$, —S(O)$_2$N(R$^3$)$_2$, —N(R$^3$)S(O)$_2$R$^3$, alkyl, haloalkyl, perhaloalkyl, alkenyl, alkynyl, cycloalkyl, heterocycloalkyl, aryl, heteroaryl, aralkyl, and —(CR$^4_2$)$_p$A, wherein p for each instance is independently a whole number selected from 1-10; R$^4$ for each instance is selected from the group consisting of hydrogen, alkyl, cycloalkyl, aryl, and heteroaryl; or two instances of R$^4$ taken together with the carbon to which they are bonded form a 3-6 membered cycloalkyl; and A for each instance is independently selected from the group consisting of halide, nitrile, nitro, azido, —OR$^3$, —SR$^3$, —N(R$^3$)$_2$, —C(O)R$^3$, —C(O)OR$^3$, —OC(O)R$^3$, —N(R$^3$)C(O)R$^3$, —C(O)N(R$^3$)$_2$, N(R$^3$)C(O)OR$^3$, —OC(O)N(R$^3$)$_2$, —OC(O)OR$^3$, —NR$^3$)C(O)N(R$^3$)$_2$, —S(O)$_2$R$^3$, —S(O)$_2$N(R$^3$)$_2$, —N(R$^3$)S(O)$_2$R$^3$, alkynyl, heterocyeloalkyl, aryl, heteroaryl, and aralkyl; or two instances of R$^2$ together with the carbons to which they are bonded form an optionally substituted 5-6 membered carbocycle; and R$^3$ for each instance is independently hydrogen, alkyl, haloalkyl, perhaloalkyl, alkenyl, alkynyl, cycloalkyl, heterocycloalkyl, aryl, heteroaryl, or aralkyl; or two instances of R$^3$ together with the atoms to which they are bonded form a 3-6 membered cycloalkyl or heterocycloalkyl.

2. The method of claim 1, wherein each instance of R$^1$ is independently selected from the group consisting of alkyl, halide, and —OR$^3$.

3. The method of claim 1, wherein each of Ar$^1$ and Ar$^2$ is:

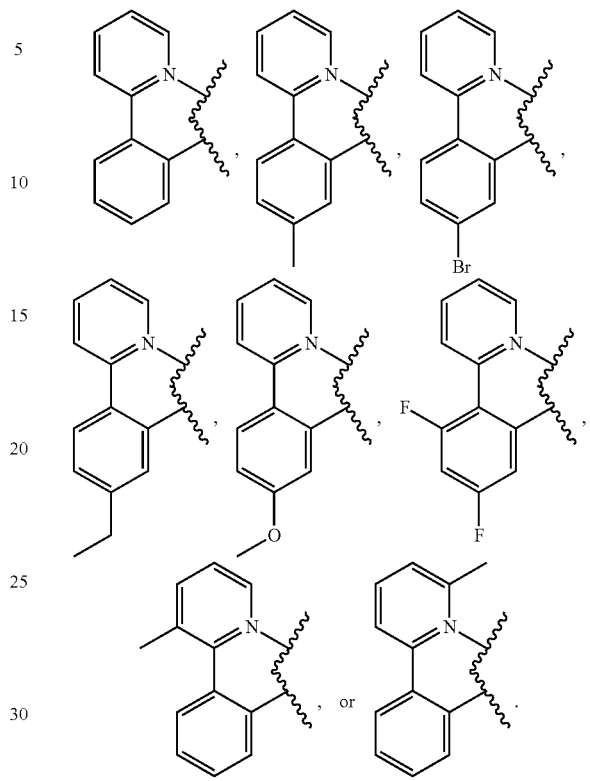

4. The method of claim 1, wherein each instance of R$^2$ is independently selected from the group consisting of alkyl, aryl, halide, nitro, —OR$^3$, —P(O)(OR$^3$)$_2$, and —C(O)OR$^3$; or two instances of R$^2$ taken together with the carbon to which they are bonded form a 6 membered cycloakyl.

5. The method of claim 1, wherein each instance of R$^2$ is independently selected from the group consisting of alkyl, halide, phenyl, and —OR$^3$; or two instances of R$^2$ taken together with the carbon to which they are bonded form a 6 membered cycloalkyl.

6. The method of claim 1, wherein Ar$^3$ is:

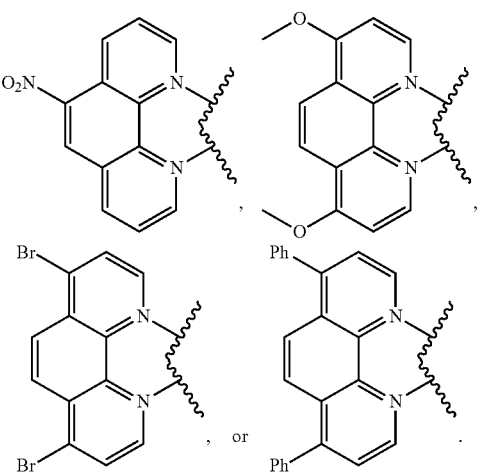

7. The method of claim 1, wherein each of Ar¹ and A² is:
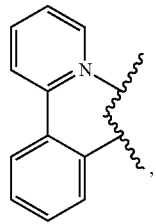 , 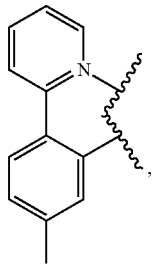 , 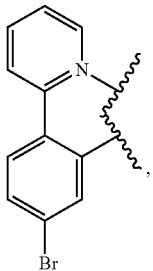 ,
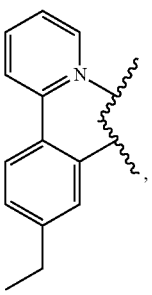 , 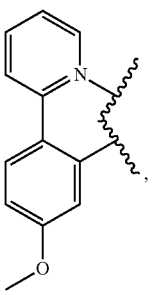 , 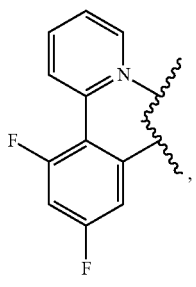 ,
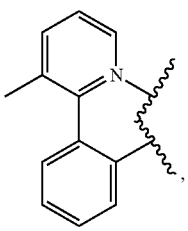 , or 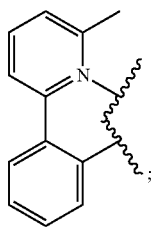 ;
and
Ar³ is:
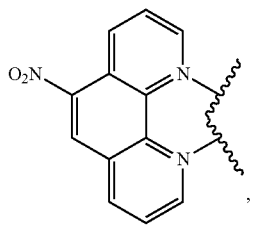 , 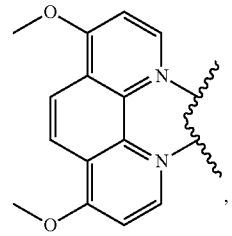 ,
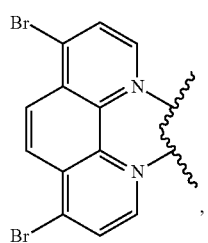 , or 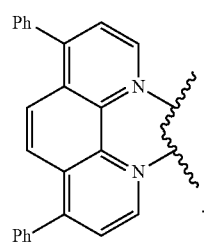 .
8. The method of claim 1, wherein the metal complex is selected from the group consisting of:
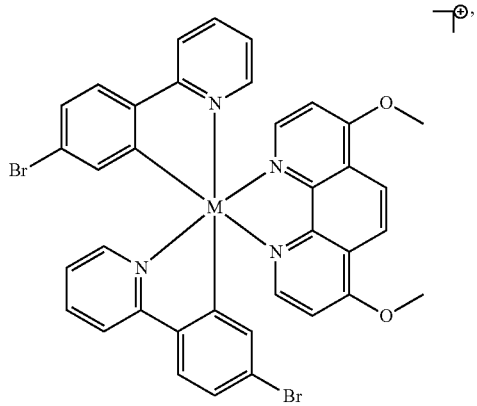
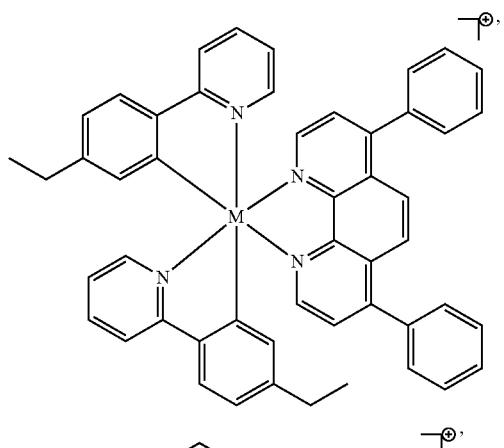
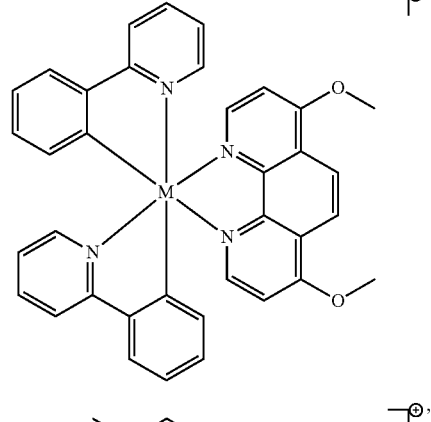
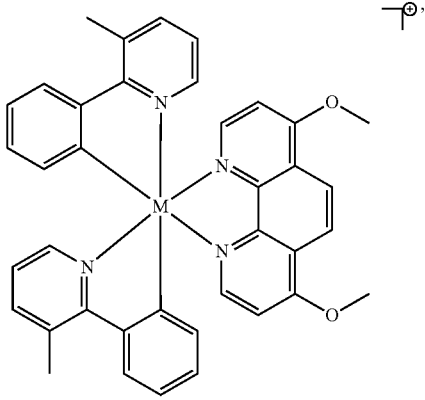

57
-continued
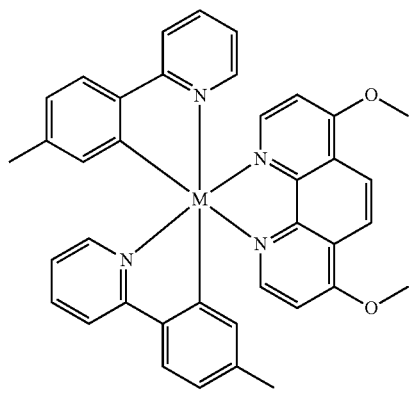
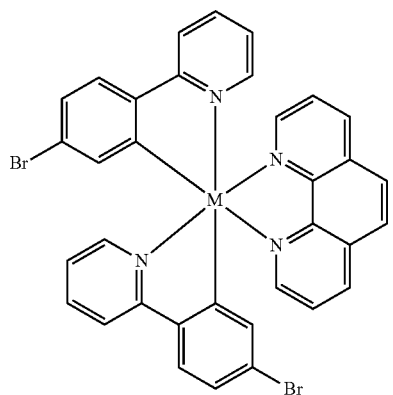
58
-continued
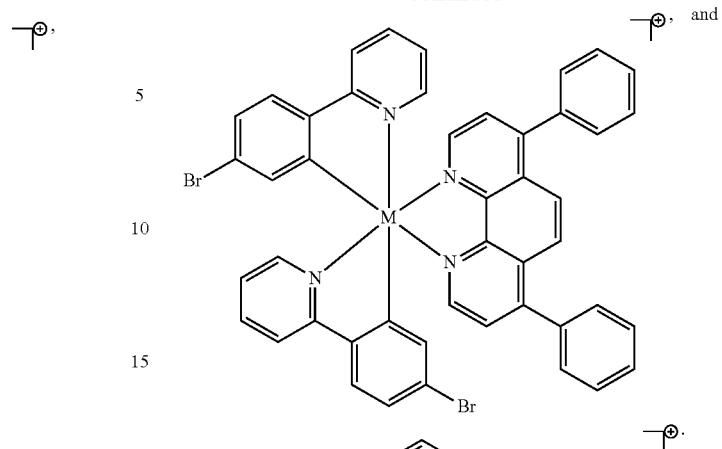
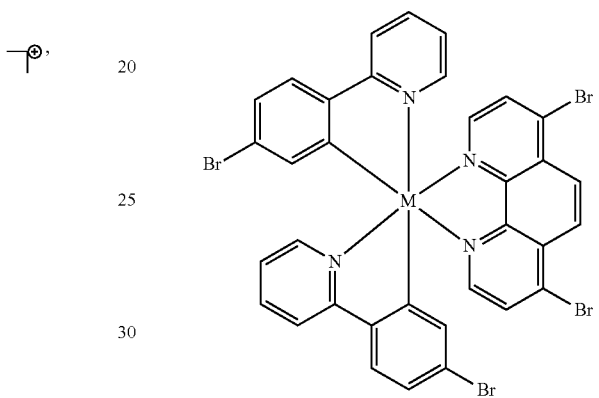
* * * * *

SEQUENCE LISTING

```
<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: Synthetic RNA, prepared in the lab

<400> SEQUENCE: 1
cugaugacca gcaacuuga                                              19

<210> SEQ ID NO 2
<211> LENGTH: 19
<212> TYPE: RNA
<213> ORGANISM: Artificial Sequence
<220> FEATURE:
<223> OTHER INFORMATION: Synthetic RNA, prepared in the lab

<400> SEQUENCE: 2
ucaaguugcu ggucaucag                                              19

<210> SEQ ID NO 3
<211> LENGTH: 19
<212> TYPE: RNA
<213> ORGANISM: Artificial Sequence
<220> FEATURE:
<223> OTHER INFORMATION: Synthetic RNA, prepared in the lab

<400> SEQUENCE: 3
uagcgacuaa acacaucaa                                              19

<210> SEQ ID NO 4
<211> LENGTH: 19
<212> TYPE: RNA
<213> ORGANISM: Artificial Sequence
<220> FEATURE:
<223> OTHER INFORMATION: Synthetic RNA, prepared in the lab

<400> SEQUENCE: 4
uugauguguu uagucgcua                                              19
```